(12) United States Patent
Nitzan

(10) Patent No.: US 11,938,085 B2
(45) Date of Patent: Mar. 26, 2024

(54) FLUID STIMULATION METHODS AND DEVICES FOR TREATING FLUID OVERLOAD

(71) Applicant: AQUAPASS LTD, Or-Akiva (IL)

(72) Inventor: Yaacov Nitzan, Hertzelia (IL)

(73) Assignee: AQUAPASS LTD, Or-Akiva (IL)

( * ) Notice: Subject to any disclaimer, the term of this patent is extended or adjusted under 35 U.S.C. 154(b) by 81 days.

(21) Appl. No.: 17/628,307

(22) PCT Filed: Jul. 17, 2020

(86) PCT No.: PCT/IB2020/000594
§ 371 (c)(1),
(2) Date: Jan. 19, 2022

(87) PCT Pub. No.: WO2021/014207
PCT Pub. Date: Jan. 28, 2021

(65) Prior Publication Data
US 2022/0257466 A1 Aug. 18, 2022

Related U.S. Application Data

(60) Provisional application No. 63/045,446, filed on Jun. 29, 2020, provisional application No. 62/957,446, (Continued)

(51) Int. Cl.
A61H 33/14 (2006.01)
A61B 5/00 (2006.01)
A61B 5/145 (2006.01)

(52) U.S. Cl.
CPC ......... *A61H 33/14* (2013.01); *A61B 5/14521* (2013.01); *A61B 5/4266* (2013.01); (Continued)

(58) Field of Classification Search
CPC ... A61B 5/015; A61B 5/14521; A61B 5/1451; A61B 5/14517; A61B 5/4266; (Continued)

(56) References Cited

U.S. PATENT DOCUMENTS 5,010,777 A * 4/1991 Yehl ........................ B60H 3/00
361/231
10,973,721 B2 * 4/2021 Fassihi ............... A61H 33/6068
(Continued)

*Primary Examiner* — Deanna K Hall
(74) *Attorney, Agent, or Firm* — Brown Rudnick LLP; Adam M. Schoen

(57) ABSTRACT

Methods for treating fluid overload in a subject comprise shifting fluids directly and non-invasively from an interstitial compartment of the subject to skin of the subject through controlled local sweating. Methods of the invention allow for removal of excess fluid from the interstitial compartment of the subject and treat fluid overload in the subject. Sweat stimulation systems comprise a chamber and first and second relative humidity sensors. The chamber is sized to fit around a body part of a subject, comprises an inlet and an outlet, and is configured such that air flows through the chamber from the inlet to the outlet. The first relative humidity sensor is operably located inside the inlet, and the second relative humidity sensor is operably located proximate the outlet.

28 Claims, 30 Drawing Sheets

Related U.S. Application Data filed on Jan. 6, 2020, provisional application No. 62/948,988, filed on Dec. 17, 2019, provisional application No. 62/943,285, filed on Dec. 4, 2019, provisional application No. 62/938,971, filed on Nov. 22, 2019, provisional application No. 62/876,381, filed on Jul. 19, 2019.

(52) U.S. Cl.
CPC .......... *A61B 5/4836* (2013.01); *A61B 5/4878* (2013.01); *A61H 2033/141* (2013.01); *A61H 2201/0207* (2013.01); *A61H 2201/025* (2013.01); *A61H 2205/083* (2013.01); *A61H 2230/505* (2013.01)

(58) Field of Classification Search
CPC ... A61B 5/4836; A61B 5/4878; A61B 5/4875; A61B 5/4881; A61H 2033/141; A61H 2201/0207; A61H 2201/025; A61H 2230/505; A61H 33/14
See application file for complete search history.

(56) References Cited

U.S. PATENT DOCUMENTS

| | | | | |
|---|---|---|---|---|
| 2005/0043595 | A1* | 2/2005 | Miller | A61B 5/4261 600/306 |
| 2006/0241549 | A1* | 10/2006 | Sunnen | A61K 33/00 604/23 |
| 2008/0275310 | A1* | 11/2008 | Kim | A61B 5/015 600/300 |

* cited by examiner

| | From inflow RH HOBO reader | | | Calculated ABH inflow gr/m3 | From Outflow RH HOBO reader | | Calculated ABH outflow gr/m3 | Air flow m3/min | sweat rate gr/hr |
|---|---|---|---|---|---|---|---|---|---|
| | time | T | rh | Absolute H | T | rh | Absolute H | | |
| 4 | 09:39 | 45.41 | 20 | 13.37010086 | 39.6 | 32 | 16.05133382 | 1.5 | 241.31 |
| 5 | 09:42 | 45.47 | 19.4 | 13.00671322 | 39.45 | 31.7 | 15.78082173 | 1.5 | 249.67 |
| 6 | 09:45 | 44.94 | 20.1 | 13.13418008 | 39.41 | 31.7 | 15.74894471 | 1.5 | 235.33 |
| 7 | 09:48 | 45.07 | 20.8 | 13.67764311 | 39.25 | 34.1 | 16.80472391 | 1.5 | 281.44 |
| 8 | 09:51 | 45.04 | 21.2 | 13.92039236 | 39.16 | 34.5 | 16.92454462 | 1.5 | 270.37 |
| 9 | 09:54 | 45.07 | 21.9 | 14.40098 | 37.99 | 37.4 | 17.28709306 | 1.5 | 259.75 |
| 10 | 09:57 | 45.07 | 21.5 | 14.13794841 | 38.01 | 38 | 17.58238031 | 1.5 | 310.00 |

FIG. 27

| Total weight change grams | weight change from sweat only grams | Calculated sweat rate full procedure g/h | T Core °C Average core Temperature °C | T Skin °C Average skin Temperature °C | HR Start BPM | HR End BPM | BP Baseline SBP0 mmHg | BP Baseline DBP0 mmHg | BP4h SBP4h mmHg | BP4h DBP4h mmHg | Blood Sodium Baseline mmol/L | Blood Sodium End mmol/L | Blood BUN Baseline mmol/L | Blood BUN End mmol/L | Blood Creatinine Baseline mmol/L | Blood Creatinine End mmol/L |
|---|---|---|---|---|---|---|---|---|---|---|---|---|---|---|---|---|
| 1.00 | 1.27 | 317.5 | 36.7 | 37.2 | 60 | 68 | 114 | 64 | 118 | 66 | 137 | 140 | 20.8 | 25 | 1.39 | 1.33 |

FIG. 28

|  | Baseline | End of Treatment | P Value |
|---|---|---|---|
| Creatinine (mg/dL) | 0.89 ± 0.15 | 0.92 ± 0.16 | 0.04 |
| BUN (mg/mL) | 14 ± 3 | 13 ± 3 | 0.005 |
| Serum Na (mmol/L) | 139 ± 1 | 140 ± 2 | 0.20 |
| Urine Na (mmol/L) | 75 ± 62 | 126 ± 62 | 0.007 |

FIG. 30

FLUID STIMULATION METHODS AND DEVICES FOR TREATING FLUID OVERLOAD

CROSS-REFERENCE TO RELATED APPLICATIONS

This application is a national stage entry of PCT/IB2020/000594 with an International Filing Date of Jul. 17, 2020, which claims priority to, and the benefit of, U.S. Provisional Application No. 63/045,446, filed Jun. 29, 2020, and to U.S. Provisional Application No. 62/957,446, filed Jan. 6, 2020, and to U.S. Provisional Application No. 62/948,988, filed Dec. 17, 2019, and to U.S. Provisional Application No. 62/943,285, filed Dec. 4, 2019, and to U.S. Provisional Application No. 62/938,971, filed Nov. 22, 2019, and to U.S. Provisional Application No. 62/876,381, filed Jul. 19, 2019, the contents of each of which are incorporated by reference herein in their entireties.

FIELD OF THE INVENTION

The invention generally relates to systems and methods of stimulating fluid transfer through the skin in a subject for treating edematous clinical conditions in the subject.

BACKGROUND

Some patients suffer from chronic pathological conditions in which there is an imbalance of fluids in the body. Congestive heart failure, for example, occurs when fluid builds up around the heart. Because of the excess fluid, the heart is unable to pump sufficiently to maintain blood flow to meet the body's needs. A person suffering from heart failure may experience shortness of breath, exhaustion, rapid heartbeat, and swollen limbs. Heart failure is a common, potentially fatal condition and is a leading cause of hospitalization in people over the age of 65.

In heart failure, the heart works harder to eject blood, leading to a buildup of blood pressure. When elevated blood pressure prevents fluids from draining from the interstitial compartments of the body, edema, or swelling caused by fluid accumulation in bodily tissues, may occur. The additional work of the heart due to edema weakens the heart, further reducing the ability of the heart to function properly. The fluid accumulation may lead to additional health conditions, hospitalization, and death.

Patients suffering from such conditions are typically treated on a daily basis by oral drugs such as diuretics and on a weekly basis in hospitals by using IV diuretics treatment. Most of those patients develop resistance to the Diuretic treatment, worsening renal function and other side effects thereby greatly reducing the efficacy of this the primary treatment option.

SUMMARY

The invention provides methods and systems that remove fluid from the body through controlled skin fluid transfer. The invention provides non-invasive methods and systems designed for treating chronic patients at home, at the clinics and in hospital thus allowing the patient to greatly reduce hospital visits and his reliance solely on pharmaceutical treatments.

Fluid flow, such as sweat flow, is directly connected to the interstitial compartment. Sweat fluid is interstitial fluid that fills the sweat gland when triggered to do so. If controlled, sweat and other fluid can be removed from the patient at a flow rate of up to 2 liters per hour. In some instances, local heat can be applied together with humidity and airflow conditions to increase rate of fluid removal or sweating.

In other instances, neural stimulation of the sweat glands can produce sweating. For example, neural stimulation may result from the use of electrodes on a body part of the patient. The electrodes deliver electrical pulses to the body part. In some embodiments, the electrodes may be disposed in a wearable cuff that fits around a body part. In some embodiments, the electrodes may be disposed in a patch that is arranged on a body part.

In some instances, creation of osmotic pressures favoring outflow of fluids from the body, other than through sweat glands, can be applied. In other instances, nutritional diet, mental parameters, or pharmacological or chemical administration can stimulate sweat production or fluid loss.

The invention provides methods and systems that remove fluid from the body through controlled skin fluid transfer, independently and regardless of pharmaceuticals, nutrition, and mental condition. Moreover, the invention provides methods for removing excess interstitial fluid by increasing sweat flow through the skin of a patient. The invention provides for removal of interstitial fluid from any part of the body, such as, but not limited to, the lower limbs, the upper limbs, abdomen, chest, or back. Other embodiments allow for removal of interstitial fluid through saliva production, which removes fluid through the mouth of a patient.

A wearable chamber is placed around a body part of the patient. To stimulate sweat production, the chamber generates heat at controlled temperatures between about 32° C. and about 50° C., controlled relative humidity equal to or less than about 85% (e.g., less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5%, including any value in between the recited values) and controlled flow rate of between about 0.2 cubic meters per minute and about 4 cubic meters per minute that stimulates sweat production. The gap between the patient body and the wearable chamber wall can be any distance, and might have direct contact in some points. The chamber can be flexible or rigid. In some instances, the chamber is completely sealed to air and humidity. In other instances, the chamber is made of membrane that allows certain evaporation of humidity and air passage.

One or more sweat content sensors determine the mineral composition within the sweat and determine what additional food supplements, if any, are needed to balance the patient status. For example, supplements may include sodium chloride, potassium, calcium, and magnesium. A remote portal or programmer allows the treatment and sweat parameters to be sent to a physician who can monitor the treatment remotely. The system includes one or more relative humidity sensors and one or more temperatures sensors at the inlet, or inlet pipe, of the apparatus and one or more sensors close to the outflow of the air in the apparatus. The system also includes one or more flow meters at the inlet on which the body part is within. The sweat rate and its accumulated amount per hour is calculated by the device as a function of the flow rate in the device multiplied by the changes of absolute humidity between the inlet and outlet of air flow. The absolute humidity is automatically calculated by knowing the relative humidity and temperature. The sweat rate is presented to the user and can be sent remotely to a treating physician.

In some embodiments, the device measures fluid loss during the treatment by measuring the patient body weight before, during, and after the treatment. One or more temperature sensors or sweat sensors might be placed on the patient body inside of the chamber, such as on a face or a neck of the patient, in order to provide a reference measure of sweat and skin temperature during treatment.

In certain aspects, the invention is directed to methods for treating fluid overload in a subject. The methods comprise shifting fluids directly and non-invasively from an interstitial compartment of the subject to skin of the subject through controlled local sweating, thereby removing excess fluid from the interstitial compartment of the subject and treating fluid overload in the subject. Sweating is stimulated by controlling relative humidity and temperature within a chamber.

Methods of the invention further comprise calculating a sweat rate within the chamber. The methods further comprise analyzing sweat content and recommending nutritional supplement. In some embodiments, the methods comprise aerobic or anaerobic exercising of a body part of the subject within the chamber to encourage sweating without increasing the core temperature of the body by more than 0.5° C. In some embodiments, the method further comprises controlling and monitoring conditions of the chamber using a controller, wherein the controller is operable by a user to program conditions of the chamber. In some embodiments of the invention, the method is carried out using a sweat stimulation system.

In certain aspects, the invention is directed to a sweat stimulation system. The sweat stimulation system comprises a chamber and first and second relative humidity sensors. The chamber is sized to fit around a body part of a subject, leaving clear volume of air between the body part and walls of the chamber, comprises an inlet and an outlet, and is configured such that air flows through the chamber from the inlet to the outlet. The first relative humidity sensor is operably located proximate the inlet, within the inlet pipe that drives the air from the heat generator to the chamber so that it can pick up all the air that flows into the chamber, and the second relative humidity sensor is operably located proximate the outlet. The heat source can be part of the chamber wall or can be placed next to the chamber wall, and the heat will be transferred to the chamber by a certain line or tubing. Similarly, the air fan can be part of the chamber wall or may be placed next to the chamber wall and transfer the air to the chamber by a certain line or tubing.

In certain embodiments, the system has a skin temperature sensor that is placed on the skin of the patient. The skin temperature sensor monitors the skin temperature and verifies that the skin temperature does not, in any circumstance, elevate above 39° C. If the skin temperature elevates above 39° C., the system stops operation of the device or reduces its inflow temperature or airflow rate. In some embodiments, the skin temperature sensor sends values to a controller, wherein the controller calculates sweat rates from humidity sensors and ensures that air flow in temperature is optimized relative to the skin temperature sensor. For example if the skin T reads 34° C. and the sweat rate is only 100 ml/hr then the controller will elevate the ambient air temperature till the sweat rate is 300 ml/hr or that the skin T has elevated over 38° C. (whichever comes first).

The system further comprises a controller communicatively coupled with a plurality of sensors that provide data to the controller for calculating sweat rate within the chamber, the controller comprising a processor configured to control and monitor conditions of the chamber and operable by a user to program conditions of the chamber. In certain embodiments, the system comprises a body scale to measure the body weight of the patient. In some embodiments, the system comprises a clock to measure the duration of the treatment.

The system further comprises an air fan coupled to the chamber. In some embodiments, the system further comprises inflow and outflow flow meters associated with the air fan. The flow meters are communicatively coupled with the controller and data from the flow meters is used for calculation of the sweat rate within the chamber. The controller is used to analyze sweat content and recommend nutritional supplement.

The system further comprises an exercise device disposed in the chamber, the exercise device for use by the patient to encourage sweating. The exercise device comprises a pedal exercise device or a spring exercise device for anaerobic exercise that will not elevate the core temperature of the body by more than 0.5° C. The body part comprises one or more legs, one or more arms, a torso, lower back, and abdomen up to the level of the chest and below the level of the heart. An interior of the chamber is configured such that walls of the chamber are kept spaced from the body part of the subject.

In some embodiments, the system comprises a blood pressure monitor, heart beat monitor, and core body gauge to monitor the patient parameters during the treatment. The system stimulates fluid loss without changing the patient blood pressure, core temperature, or heartbeat. In certain embodiments of the invention, the chamber is fixed to a surface, such as a bed or chair. In other embodiments, the chamber is mobile or wearable by a patient.

In such a system, an apparatus such as a cuff or chamber that creates a controlled temperature, pressure, and humidity environment can be placed on a patient's arm, leg, abdomen, back, or a combination thereof. The chamber can be worn at home for about a few hours. Wearing the chamber for the short duration will result in sweat formation from the heat generated.

The sweat can be monitored, and its content collected and evaluated to assess the edema status and to determine if the patient needs to take supplements, such as minerals or other additives, to preserve correct blood count. The chamber can generate results of the fluid removal, including sweat content status and heat generation, for display on a user interface or for transmitting to network for monitoring by a physician that is remote. The patient can apply the treatment for duration throughout the day, at home, and use the treatment to balance fluid status.

In certain embodiments, devices of the invention further comprise a system that records treatment parameters and results. The system is configured to transfer the data by wireless or any other communication method to a medical center for analysis and control.

In some aspects, the invention provides a fluid removal treatment device that a patient can use on the go or from the comfort of their own home. In particular, some embodiments of the invention provide a portable device that can be worn for a few hours or may be worn overnight to remove excess interstitial fluid by inducing sweat. The device comprises an apparatus such as a cuff, chamber, or sleeve that creates a controlled environment around the patient's body part, such as, an arm, leg, abdomen, back, or a combination thereof. In certain instances, the device can be used to reduce afterload by heating and increasing cutaneous vascular conductance. As such, using the device overnight is useful for treating dyspnea and/or orthopnea to improve sleep. In some embodiments, the invention provides a mobile apparatus such as a cuff, chamber, or sleeve that a patient can wear around a body part to stimulate fluid loss while the patient is moving around. The apparatus may be designed to allow freedom of movement so that the patient wearing the apparatus can, for example, cycle or jog in it. The apparatus may be worn to improve exercise tolerance and health status of patients by reducing breathlessness. In some instances, the apparatus is sized for wearing underneath the patient's clothes so that it is less apparent.

In some embodiments, the chamber is a rigid or flexible cuff that fits around one or two legs, one or two forearms, an abdomen, or a back of a patient. One side of the cuff has an entrance to relatively dry air supply. The air humidity is monitored at the inflow, and air at temperatures ranging from about 32° C. to about 50° C. at a relative low humidity of less than about 85% are fanned into the cuff. The relative low humidity may, for example, be about 85%, 80%, 75%, 70%, 65%, 60%, 55%, 50%, 45%, 40%, 35%, 30%, 25%, 20%, 15%, 10%, or 5%. The outlet for the air is at a torso or a lower back of the patient, and the air outlet is monitored by a relative humidity sensor. The sweat amount can be calculated and displayed on a user interface. The sweat amount, or sweat rate, calculated is the difference between the absolute humidities at the inflow and the outflow multiplied by the airflow rate.

In some embodiments, the chamber is sized to fit around a patient's abdomen, one or two legs, one or two arms, a back, or any combination thereof. In some instances, the chamber may cover a substantial portion of the patient's body below the chest, for example, covering around 1 square meter of surface area and providing fluid loss at a rate of approximately 200 ml/hr. The patient can request, or be prescribed, a certain amount of fluid skin transfer per treatment. The systems of the invention will calculate sweat rate, display, and stop the operation of the system once the desired sweat amount is obtained. Calculation can be performed using input from the two humidity sensors and their difference in readings over time, such as every few minutes.

In other instances, creation of an osmotic pressures favoring outflow of fluids from the body, not through sweat glands, can be applied. For example, in some embodiments, the fluid can be stimulated by a chamber that has a wet environment with specific and controlled mineral content, primarily salts and electrolytes such as sodium potassium and chloride. The mineral content drives fluids out of the body by the mechanism of osmosis and also balances the electrolytes and mineral composition of the fluids as required in the body.

In some embodiments, the invention is directed to a method of removing fluids through the skin by osmosis. The method comprises fitting a chamber around a body part of a patient, the chamber comprising interstitial electrolytes. The method further comprises controlling content and concentration of the interstitial electrolytes in the chamber, thereby driving water and salts out of the body part of the patient while maintaining pH and electrolyte levels of the body part.

In some embodiments of the invention, fluid loss may comprise saliva generation. The saliva glands can produce up to about 2.5 liters of fluid per day. Stimulation of saliva glands can be achieved by chewing gum or any other material suitable as a stimulator. The saliva can be collected, measured, and analyzed. The system might have a flavor, such as a flavored mouthpiece, that will stimulate production of saliva.

In certain embodiments, the invention is directed to a fluid loss stimulation device comprising a housing. The housing comprises a mouthpiece, a storage chamber, and suction. The mouthpiece is disposed at a proximal end of the housing. The device comprises a power button for providing power to the suction. For example, battery power may be used to power the suction, which may be any suitable suction component, such as a pump. The suction is configured to deposit saliva from a mouth of a patient into the storage chamber of the device. The storage chamber is removably detachable from the device. For example, the storage chamber may comprise a threaded end that is couples with threads on a body of the device. Rotation of the storage chamber results in detachment of the threaded components.

Another aspect of the invention is based on the recognition that it may be important to maintain a balanced level of sodium in the body while fluid is removed from the body during the sweating process or also when trying to maintain electrolyte balance of a patient suffering from imbalances of the electrolytes in the body especially potassium, sodium, chloride and carbonate. Sweat is isotonic in the sweat gland. As sweat moves through the skin and out of the body, a portion of sodium from the sweat is re-absorbed back into the body to maintain a proper salt balance in the body. However, in certain instances, the induction of sweating can lead to salt imbalance since water is driven out of the body while sodium is re-absorbed. Methods and systems of the invention thus include the insight to prevent this imbalance by introducing negative ions into the airflow. When negative ions are introduced into the airflow, sodium, which is positively charged, is driven towards the skin surface by the ion bond strength and as a result re-absorption decreases, thereby preventing a salt imbalance.

In certain aspects, methods and systems of the invention provide a fluid stimulation system with a chamber sized to fit around a body part of a subject to stimulate fluid loss. The chamber is sized to leave a clear volume of air between the body part and walls of the chamber. The chamber further includes an inlet and an outlet and is configured such that an air flow passes through the chamber from the inlet to the outlet whilst circulating evenly throughout the body surface. The air flow includes negative ions introduced by a component of the system. For example, one of carbonate, sulphate, bromide, chloride, fluoride, iodide, nitride, oxide, or sulfide ions may be introduced into the airflow by the component of the system. In certain instances, the component is an ion resin located near the inlet of the chamber. Alternatively, the component is a negative ion generator that is located at the inlet of the chamber. Introducing negative ions into the fluid stimulation system is useful for inhibiting sodium re-absorption during fluid loss, thereby preventing a salt imbalance. Such methods may involve introducing negative ions (e.g., one of carbonate, sulphate, bromide, chloride, fluoride, iodide, nitride, oxide, or sulfide ions) into the airflow to inhibit sodium re-absorption during sweating.

In other instances when the electrolyte balance is such that the patient has hyponatremia, positive ions (cations) will be dissolved into the humid air flow (relative humidity between 40%-85% to enable maximal amount of cations to be dissolved in the water molecules in the air). This way when the patient sweats the sodium will repel the sodium flowing to the surface and increase the sodium concentration in the interstitial compartment and then in the plasma.

In other aspects, this disclosure provides methods and devices to reduce edema by enhancing fluid transfer through the skin while maintaining patient mobility.

For example, in some embodiments this disclosure provides a mobile system. The mobile system comprises a wearable capsule and a console, to elevate skin temperature so as to initiate sweat production. For example, a wearable device may be provided to create a warm air environment at a predetermined volume around the body to initiate sweat production and reduce symptoms of edema. Methods and devices may be controlled by smartphone application.

In some aspects, this disclosure provides a method to reduce Orthopnea and Paroxysmal Dyspnea (PND) shortness of breath and enable supine position sleeping and/or enhanced diuresis when laying down. The method preferably reduces blood pressure and enables diaphragm full inspiration stretching.

In some instances, this disclosure may provide an apparatus that increases a temperature at a part of portion of a subject's body to create vasodilation of the vasculature, thereby reducing pressures and alleviating symptoms such as a shortness of breath. Devices of the invention may provide an apparatus that pushes the abdomen away from the diaphragm by actively pressing or pulling the abdomen towards the pelvis.

In yet another aspect, this disclosure may provide a method to reduce sodium concentrations in the plasma and interstitial compartment by enhancing sweat rate and drawing to a surface of skin sodium cations. The sweat may be drawn to the surface of the skin with air comprised of negatively charged anions.

In other aspects, disclosure provides an apparatus for enhancing sweat with warm air that is delivered into a wearable apparatus around a subject's body. Delivering the warm air into the wearable apparatus may result in elevated skin temperatures to levels of between about 33-39 degrees Celsius. In some instances, the invention provides for a warm humid air inline pipe comprising two-stage disposable apparatus. A first stage may comprise a disperser that dispenses a soluble salt into the humid air. Preferably, as the air flows through the disperser, the air becomes full with ions. A second stage may be configured to pass the ion filled air through a cation resin filter. The warm air that exits the filter and flows around the skin will be negatively charged at huminites of, for example, around 50. This air when flowing around the sweating skin will pull the sodium ions to the skin surface and reduce its reabsorption In yet other aspects, this disclosure provides a method for removing fluid overload from the interstitial and intravascular compartments by promoting fluid flow from eccrine sweat glands and out of the skin by elevating body skin temperature. Alternatively, or in addition to, this disclosure provides a method for controlling skin temperature and sweat rate by closing a control loop inputting relative humidity at the inflow and the outflow, the air flow rate and the skin temperature and changing the flow rate and inflow air temperature until a sufficient sweat rate is achieved. The apparatus may have a weight built in that inputs the baseline and final weights to the system that can then send the information, for example, by the internet, to the treating physician. The apparatus may be worn around a body part, for example, from the chest and upper back down to the feet and toes. The apparatus may enable free flow of air inside the apparatus and evaporate all the sweat as it increases the air flow rate to ensure that the relative humidity is less than 70%. The apparatus may have a cross section with a mesh fabric that contacts the skin at very small area thus enabling free flow and sweat evaporation in maximal areas. The apparatus may have an airflow dispersion system incorporated inside the mesh that spreads the air evenly in the wearable thus ensuring homogenous temperatures around the body and by such optimizing total sweat rate.

BRIEF DESCRIPTION OF THE DRAWINGS

FIG. 27 shows an exemplary calculation performed from the online humidity sensors and the air flow meter.

FIG. 28 shows results a patient treatment.

FIG. 30 shows clinical data from six treated subjects.

DETAILED DESCRIPTION

Figure 1:
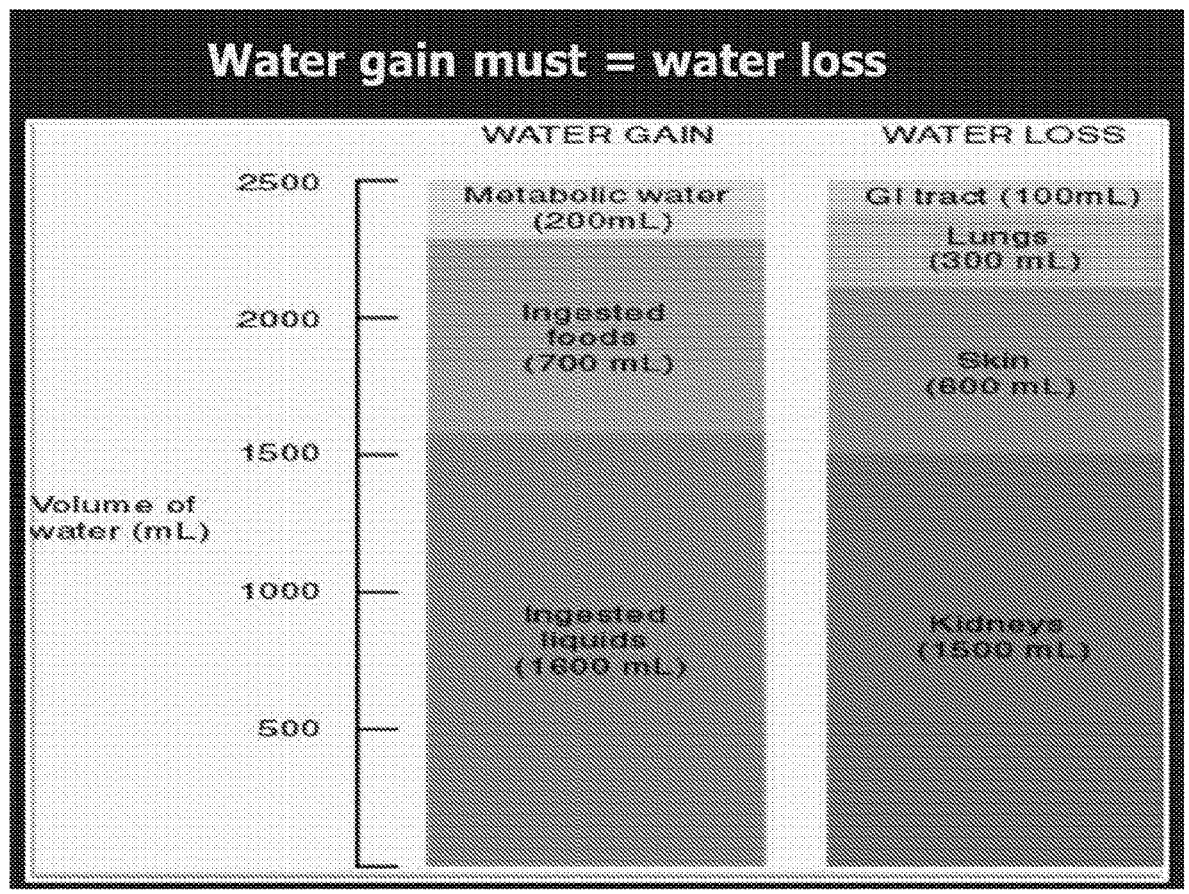
FIG. 1 is a diagram of the relationship between water gain and water loss in the body.

The invention provides methods and systems for removing excess fluid in a patient by using externally stimulated and increased sweat rates. Systems of the invention include a home-use, an outpatient clinic or in hospital device for chronic patients that need to decongest fluid overload. The device is easily adjustable between treatment areas, is easy to operate and monitor, and is easy to clean and maintain. Embodiments of the device are portable, although the device can be static during treatment episodes.

The invention also allows for reading and monitoring of fluid removed, as well as the contents of the fluid. Treatment episodes can be local and isolated to body parts such as the leg, arm, abdomen, and back and can also be applied to combination of the body parts such as the legs, torso, back and abdomen. Sweating can be regulated during treatment to allow for fluid flow from the skin of 500-2000 milliliters per day. The invention allows patients to ensure no skin or other heat injuries occur during the treatment and there are no unacceptable losses or concentration gain of electrolytes or salts that cannot be reabsorbed or digested back. Moreover, sweating is a process that most patients typically have experienced, and adverse effects to the skin are unlikely, even in severe heart failure patients.

Fluid transfer from the interstitial and intravascular compartment can be stimulated and enhanced via sweat, osmosis, other fluid transfer, or a combination thereof using local elevation of skin temperatures or increase in ambient osmotic pressure favoring fluid transfer from the interstitial compartment to outside the body.

In some embodiments, neural stimulation of the sweat glands can produce sweating. For example, neural stimulation may result from the use of electrodes on a body part of the patient. The electrodes deliver electrical pulses to the body part. In some embodiments, the electrodes may be disposed in a wearable cuff that fits around a body part. In some embodiments, the electrodes may be disposed in a patch that is arranged on a body part. The electrodes may provide stimulation of nerves, such as peripheral nerves. Any suitable electrodes may be used, such as electrodes produced by MicroProbes for Life Science (Gaithersburg, Maryland, USA).

In some embodiments, creation of osmotic pressures favoring outflow of fluids from the body, other than through sweat glands, can be applied. In other embodiments, nutritional diet, mental parameters, or pharmacological or chemical administration can stimulate sweat production. Examples of pharmacological or chemical products include zinc supplements and neuropsychiatric drug desipramine, such as NORPRAMIN (manufactured by Sanofi-Aventis U.S. LLC, Bridgewater, New Jersey, USA) may induce sweating.

Sweat rates, when the skin is exposed to local, tolerable temperature elevations of about 1° C. to about 10° C. elevating it to levels between 32° C. to 40° C., can be in the rate of about 0.5 milligram per $cm^2$ per minute. Such a rate translates to a sweat rate of over about 200 milliliters/hour from body parts having a surface area of around 10,000 $cm^2$ which is the average body surface area of both legs torso. The sweat rate is calculated using the following formula.

sweat rate=(absolute humidity out−absolute humidity in)×airflow

The invention may be used for patients of different ages. As reported in a study from Miranda A. Farage et al., Textbook of Aging Skin, thermoregulation effects were evaluated for a group of younger subjects (21-39 years in age) and a group of older subjects (61-73 years in age). Sweat responses, esophageal, skin temperatures, non-evaporative heat exchange, heart rate, cardiac output, blood pressure, forearm blood flow, and metabolic heat production were examined after exposing the subjects to 40° C. and 40% relative humidity for up to 130 minutes. The study reported that there was no significant difference in sweat rate or onset of sweating between the groups. Therefore, with age, sweat rates and changes with sweat rates can still be high enough to promote decongestion treatment in patients chronically overloaded with fluid.

Sweat rate is typically not affected by medical conditions such as congestive heart failure (CHF). Furthermore, sweat rate is not reduced in CHF patients. Sweat rate may even be higher in CHF patients because SSNA activity is not altered compared to a control. Whole body heating induces significant sweating responses, while the sweat rate toward the end of a moderate whole body heating in CHF patients is marginally lower (~20%) than that of control subjects. In CHF patients, SSNA and sweat rate increased during the initial period of whole body heating (e.g., internal temperature increase ~0.2-0.3° C.), while neither increased in healthy controls during this period.

However, cutaneous vascular conductance is reduced in heart failure patients, and skin can be more vulnerable to heat injury if exposed to heat exposure that is too high or too long in duration. CHF compensatory mechanisms typically do not allow too much peripheral vasodilation in an attempt to preserve cardiac output to vital organs. In some aspects of the invention, a skin temperature sensor determines the inflow air temperature and rate thus the ambient air temperature surrounding the skin. In cases where the CVC is markedly reduced it will not effect neither sweat rates nor the safety of the procedure as the required skin temperature will be achieved at a lower inflow air temperature and the onset of sweating will be at a lower ambient temperature. The skin temperature will always be maintained below 39° C. and so sweat rates and safety will be preserved even if CVC is reduced. Cutaneous vasodilation evoked by heat exposure may decrease afterload, and in turn improve vasodilatory response to stress. In CHF patients, reductions in cardiac output lead to an increase in vascular resistance, which may adversely affect the ability of the peripheral vascular to dilate in response to heat and exercise stress. Warm temperatures may beneficially affect peripheral resistance and cardiac output in CHF subjects and may be responsible for lower death rates during summer months. Studies have suggested that thermal therapy, such as a warm water bath, sauna, or dry sauna, can be considered in CHF subjects to increase cardiac output and ejection fraction, and improve left ventricular function, endothelial function, and the quality of life in CHF patients.

The content of sweat is derived from the content of interstitial fluid, which is mostly water. Sweat is hypotonic, with electrolytes and salts, some of which are reabsorbed. Throughout therapy, the sweat content can be monitored to ensure that there is not too much loss of electrolytes and salts in the patient.

In the invention, local heat provides an environment that allows for sweating of the body part where sweat evaporates quickly from the skin and the environment keeps the skin moist and well-nourished during the procedure. Sweat can be stimulated to result in a local limb fluid removal rate of over about 100 milliliters/hour. Treatments for the local body part can be short in duration and administered throughout the day, resulting in treatment of about a few hours overall in a day.

Water is an important part of the body and of bodily functions. In the body, fluid typically does not accumulate because water gain is typically equal to water loss. As shown in FIG. 1, for a 2500 mL volume of water, water gain occurs through metabolic water (200 mL), ingested foods (700 mL), and ingested liquids (1600 mL), while water loss occurs through the GI tract (100 mL), lungs (300 mL), skin (600 mL), and kidneys (1500 mL).

Figure 2:
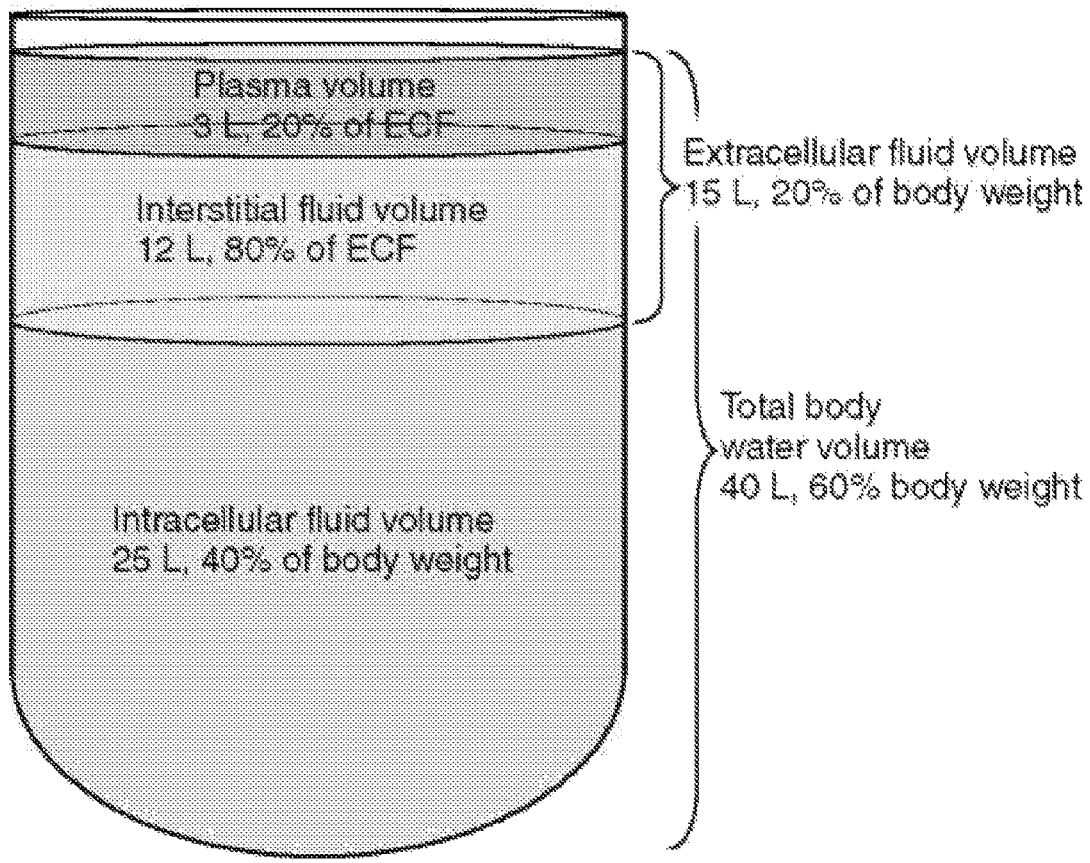
FIG. 2 is a diagram of the relationship of fluid compartments of the body.

Total body water volume is typically 40 L and accounts for 60% of body weight. Normal fluid compartments in the body include extracellular fluid (ECF) volume (15 L, 20% of body weight) and intracellular fluid volume (25 L, 40% of body weight). The ECF includes plasma volume (3 L, 20% of ECF) and interstitial fluid volume (12 L, 80% of ECF). FIG. 2 shows a diagram of the relationship of fluid compartments of the body.

Figure 3:
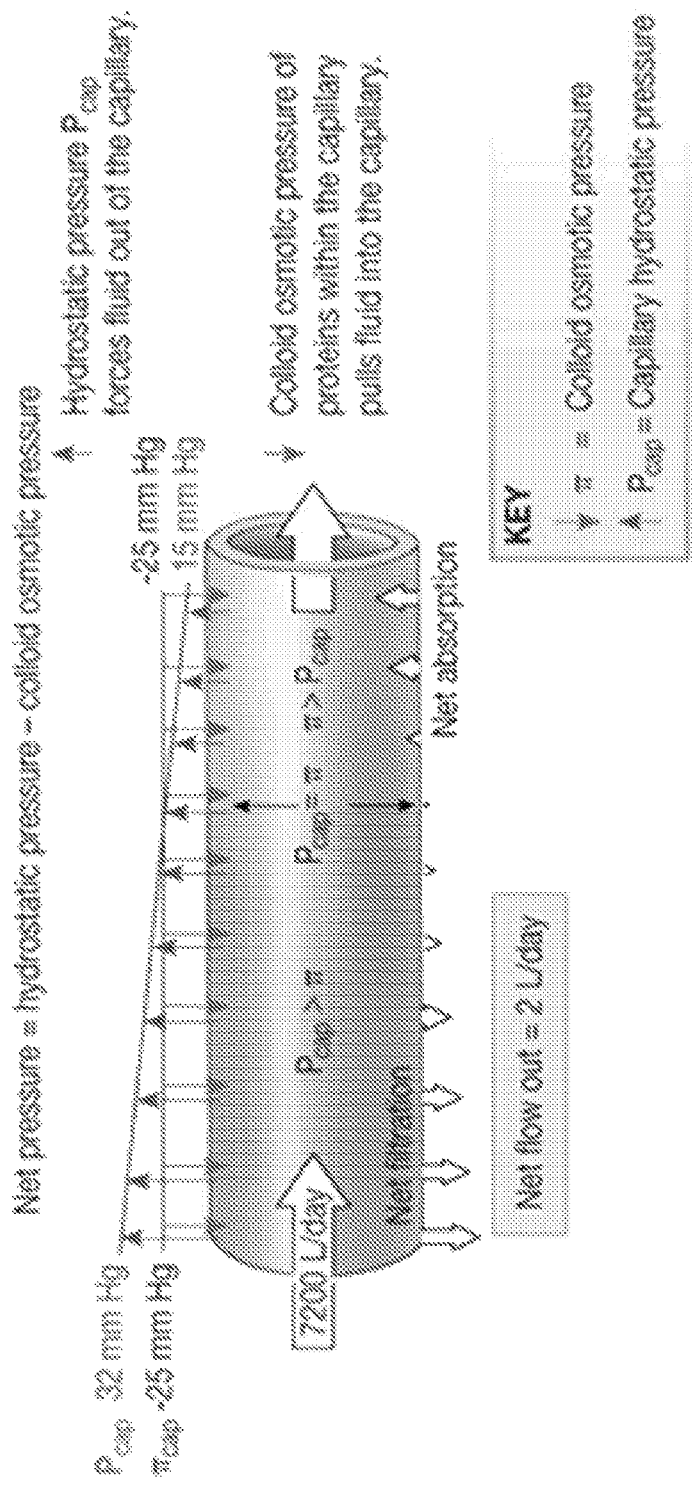
FIG. 3 is a diagram of filtration in systemic capillaries.

In the body, fluid transfer happens across capillaries. Fluid is filtered from the arterial side of capillaries to the interstitial compartment at a rate of about 22 L/day. FIG. 3 shows a diagram of filtration in systemic capillaries.

Figure 4:
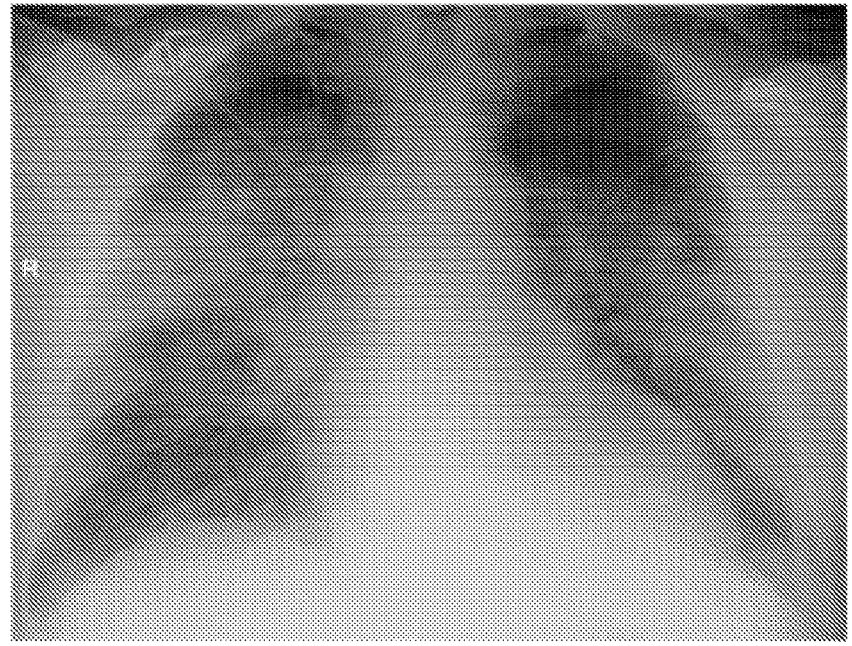
FIG. 4 is an image of a medical condition with excess fluid in the chest.
Figure 5:
FIG. 5 is an image of a medical condition with excess fluid in the legs.

In some medical conditions, such as those shown in FIG. 4 and FIG. 5, patients suffer from elevated capillary hydrostatic pressure, which leads to accumulation of fluids in the interstitial compartment. Blood flow to the skin may also be reduced.

Conventional therapies for prevention of fluid overload are directed to reducing intravascular pressure by reducing blood volume. Diuretic pills increase urine output, which leads to reduced intravascular volume and pressure. With time, patients respond less well to diuretic therapy and renal function is reduced. Patient prognosis is poor, with close to 50% not surviving more than five years after first diagnosis.

Methods of the invention can be administered alone or in combination with diuretics to improve the outcome. The invention provides systems and methods for treating fluid overload in a patient by removing excess fluid with controlled skin fluid transfer.

Sweating is one way the body releases fluids. Sweat pathways include eccrine glands or major sweat glands located throughout the entire body. Eccrine glands can secrete up to 2 L/hour of fluids directly from the interstitial compartment, and total body fluid loss from sweat can be more than 10 L/day. Sweat is 98-99% water with some electrolytes, such as sodium and chloride. Sweat also contains sodium chloride (NaCl), fatty acids, lactic acid, citric acid, ascorbic acid, and urea. Sweat is hypotonic at the skin surface and is a clear, odorless acid having pH that ranges from about 4 to about 6.8.

The hypothalamus regulates sweat and homeostasis. The hypothalamus senses a rise in temperature and sends signals via the nervous system. Sweat glands receive the signals and secrete sweat. Blood vessels receive the signals and dilate. The sweat secretion and blood vessel dilation lead to homeostasis where the internal body temperature is about 36° C. to about 38° C. In the body, the antidiuretic hormone (ADH) enhances fluid retention by making the kidneys reclaim more water. The release of ADH is triggered when osmoreceptor cells in the hypothalamus detect and increase in the osmolarity of the blood. Homeostasis is achieved by encouraging thirst, as drinking reduces blood osmolarity to a set point, and increased permeability, as water reabsorption helps prevent a further osmolarity increase. Furthermore, the renin-angiotensin-aldosterone system (RAAS) leads to an increase in blood volume and pressure to achieve homeostasis. The juxtaglomerular apparatus (JGA) responds to low blood volume or blood pressure, such as from dehydration or loss of blood. The JGA produces renin which leads to angiotensinogen and angiotensin II, which leads to arteriole constriction. Angiotensin II is also detected by the adrenal gland, which in turn produces aldosterone, leading to increased sodium and water reabsorption in distal tubules.

Figure 6:
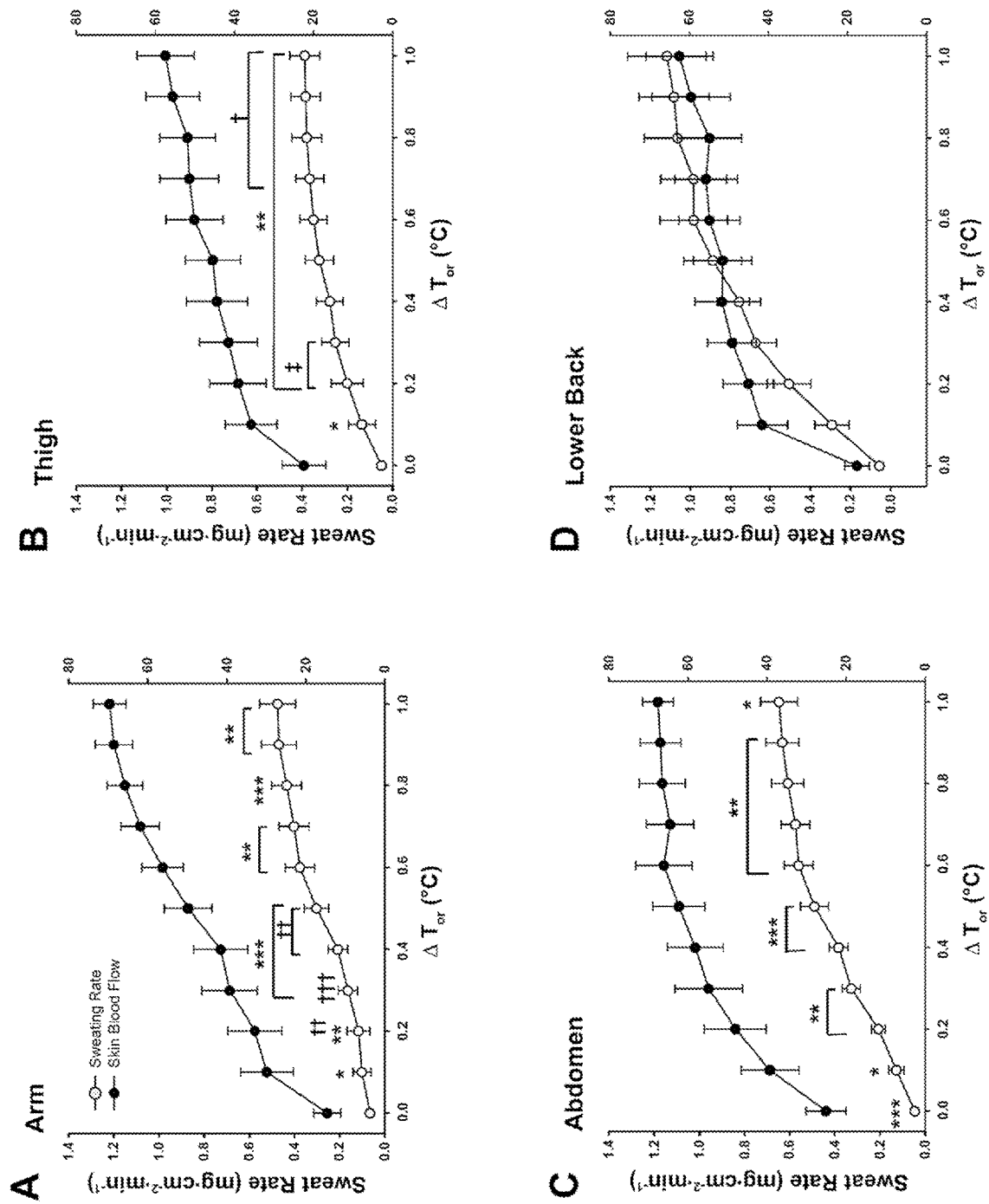
FIG. 6 shows sweat flow from A) arm, B) thigh, C) abdomen, and D) lower back) when subjected to local heat elevation.
Figure 7:
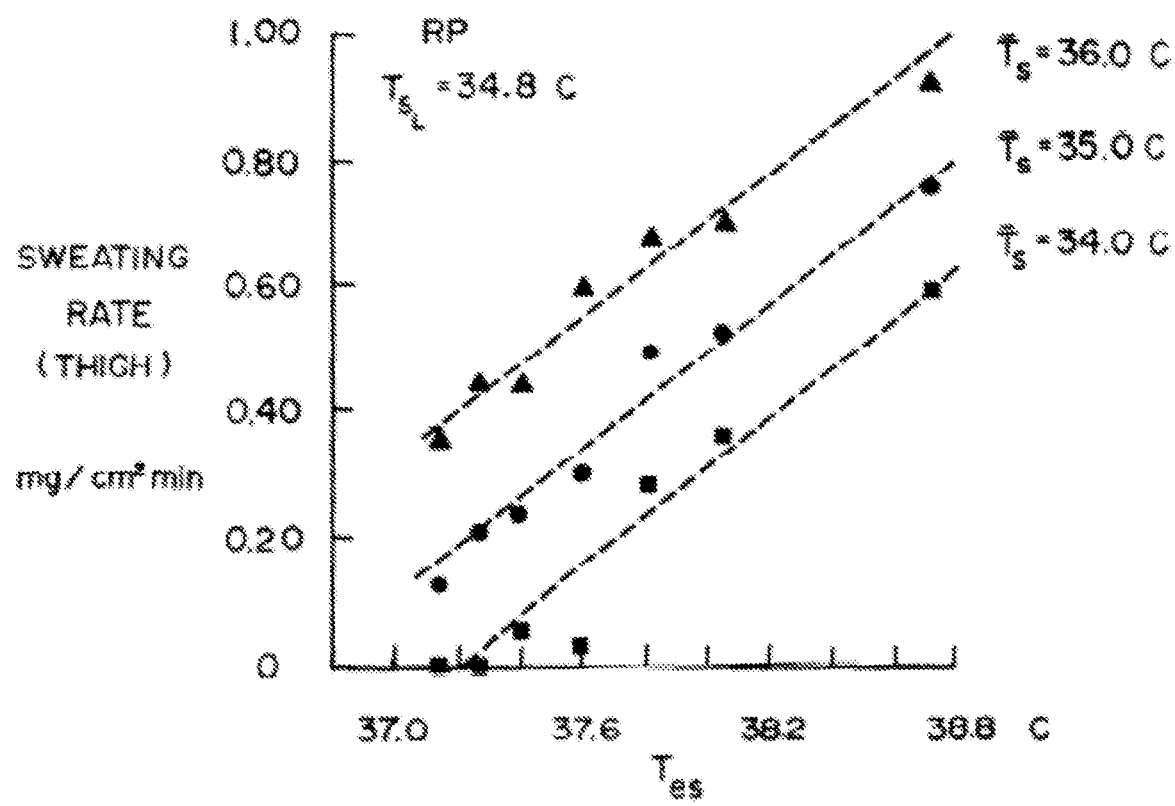
FIG. 7 shows effects of internal and average skin temperatures on local sweating rate.
Figure 9:
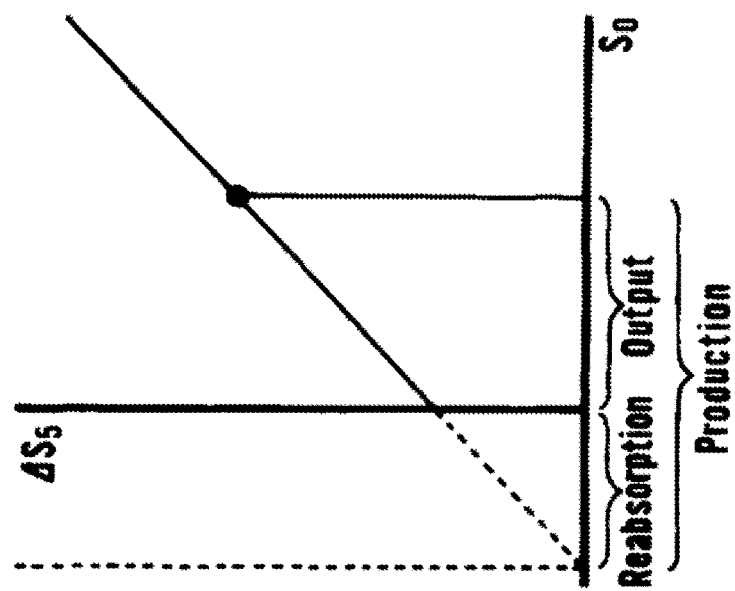
FIG. 9 is a plot of sweat rate increase to basal rate of sweat production.
Figure 8:
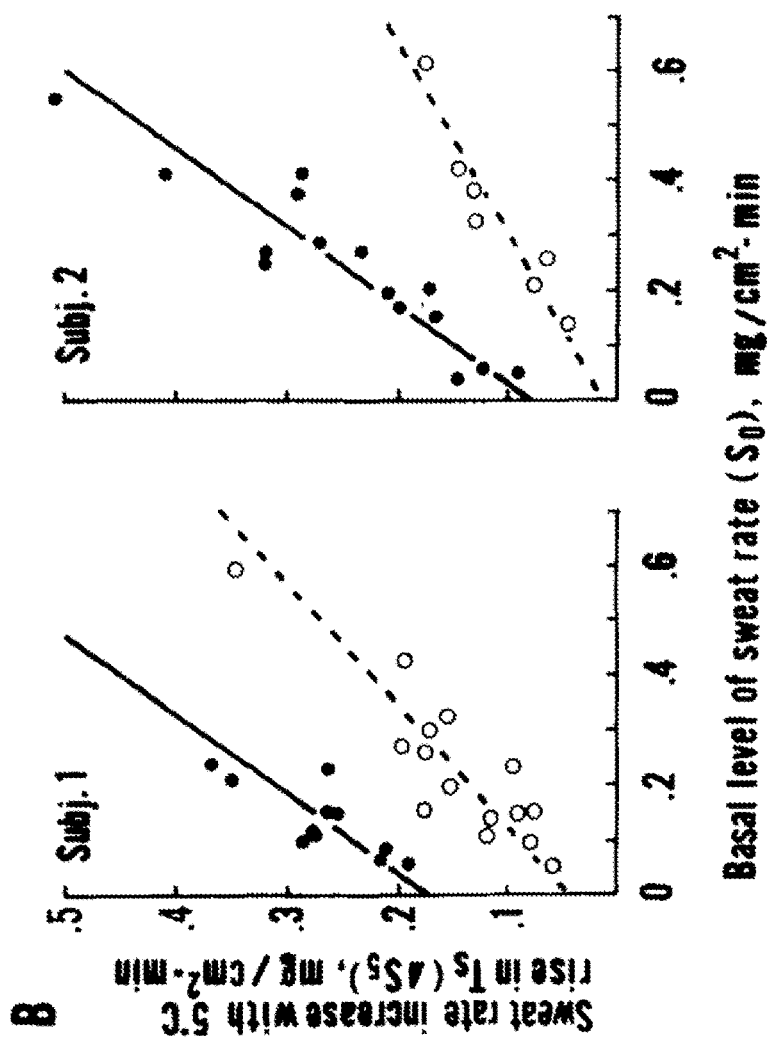
FIG. 8 shows plots of sweat rate for two subjects.
Figure 10:
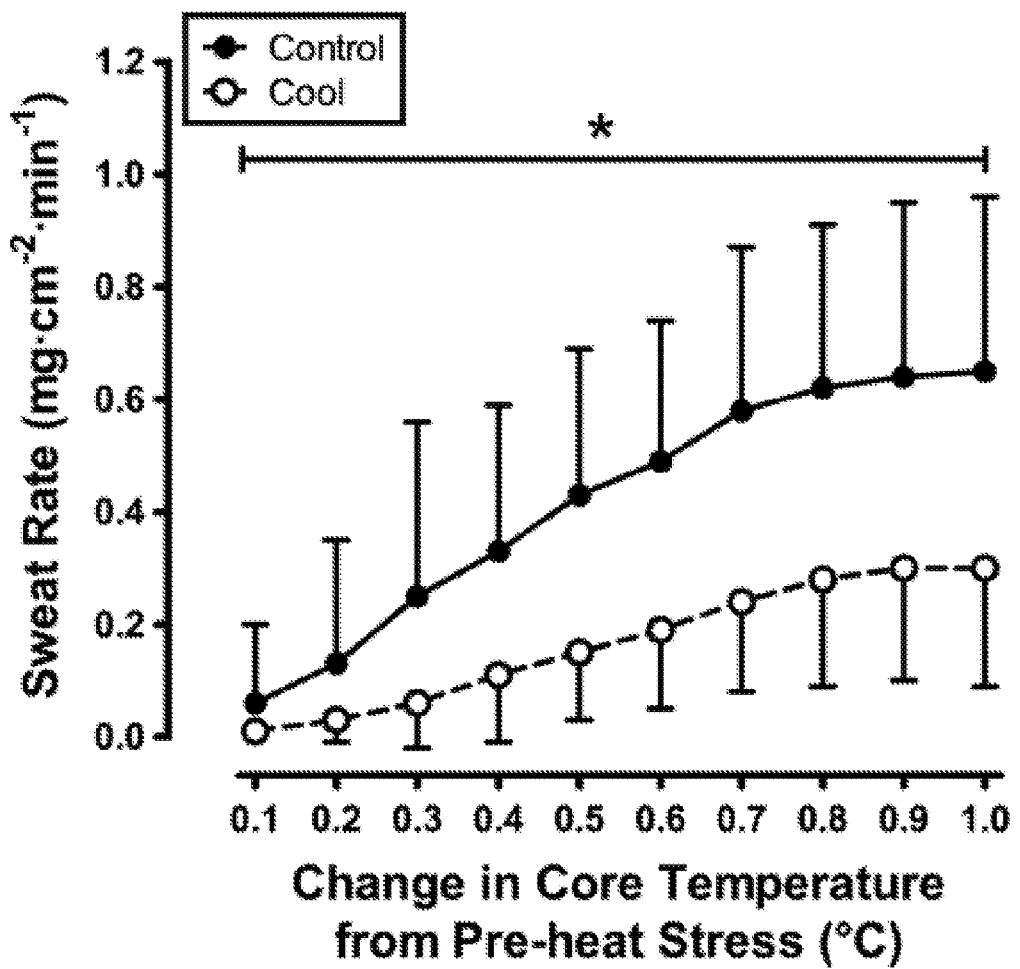
FIG. 10 shows sweat rate as a change in core temperature from pre-heat stress.

Providing a controlled environment can lead a patient to produce sweat. One way to increase sweat production is to elevate the local skin temperature for the patient. FIG. 6 shows sweat flow from specific organs (A: arm, B: thigh, C: abdomen, and D: lower back) subjected to local heat elevation. FIG. 7 shows a plot of the effect of $T_{es}$ (internal temperature) and $\overline{T}_s$ (average skin temperature) on local sweating rate with local (under sweat collection capsule) skin temperature equal to 34.8° C. FIG. 8 shows plots of sweat rate for Subject 1 and Subject 2 that increase against the basal level of sweating for the two subjects, as reported in a study with an increase in sweat rate with 5° C. rise in skin temperature by local irradiation. Solid circles denote thermal sweating and open circles denote drug-induced sweating. FIG. 9 is a plot showing that sweat rate increase is proportional to basal rate of sweat production, as reported in a study with an increase in sweat rate with 5° C. rise in skin temperature by local irradiation. FIG. 10 shows sweat rate as a change in core temperature from pre-heat stress. As the change in core temperature from pre-heat stress increases, the sweat rate increases.

Methods of the invention allow fluids to shift directly and non-invasively from the extracellular compartment to the skin by controlled local sweating or in conjunction with osmotic regulation. Additional fluid output from sweat a few times per day is beneficial in avoiding edema formation. For example, fluid output may be in the range of about 100 milliliters/hour to about 300 milliliters/hour. Vasodilation of the skin area under high temperatures will increase blood flow to the skin and the result of vasodilation will also assist in pathologies requiring enhanced blood flow.

The invention provides ergonomic, easy to use sweat stimulators. In some instances, the sweat stimulators are designed to fit around limbs, such as one or more arms or legs, a torso, abdomen, or lower back. Regulation of the local skin heat, oncotic pressure gradients, and evaporation rates of targeted organs accelerates fluid transfer through skin and reduces local edema. Moreover, the sweat content can be monitored and supplements can be given, if needed.

In certain aspects, the invention is directed to fluid stimulation systems or sweat stimulation systems comprising a chamber and first and second relative humidity sensors. The chamber is sized to fit around a body part of a subject, leaving clear volume of air between the body part and walls of the chamber, comprises an inlet and an outlet, and is configured such that air flows through the chamber from the inlet to the outlet. The first relative humidity sensor is operably located inside the inlet air pipe leading the air into the chamber. The inlet pipe drives the air from the heat generator to the chamber so that it can pick up all the air that flows into the chamber. The second relative humidity sensor is operably located proximate the outlet.

The system further comprises a controller communicatively coupled with a plurality of sensors that provide data to the controller for calculating sweat rate within the chamber, the controller comprising a processor configured to control and monitor conditions of the chamber and operable by a user to program conditions of the chamber. The controller is also used to analyze sweat content and recommend nutritional supplement.

A heat source can be part of the chamber wall or can be placed next to the chamber wall, and the heat will be transferred to the chamber by a certain line or tubing. Similarly, the air fan can be part of the chamber wall or may be placed next to the chamber wall and transfer the air to the chamber by a certain line or tubing.

The system further comprises a gas mixture with or without air. The system further comprises an air fan and heat source coupled to the chamber. The system further comprises an inflow flow meter associated with the air fan. The flow meter is communicatively coupled with the controller and data from the flow meters is used for calculation of the sweat rate within the chamber.

In certain embodiments, devices of the invention further comprise a system that records treatment parameters and results. The system is configured to transfer the data by wireless or any other communication method to a medical center for analysis and control.

In some embodiments, the system comprises a blood pressure monitor, heart beat monitor, and core body gauge to monitor the patient parameters during the treatment. The system stimulates fluid loss without changing the patient blood pressure, core temperature, or heartbeat. In certain embodiments of the invention, the chamber is fixed to a surface, such as a bed or chair. In other embodiments, the chamber is mobile or wearable by a patient.

In certain embodiments, the system comprises a body scale to measure the body weight of the patient. In some embodiments, the device measures fluid loss during the treatment by measuring the patient body weight before, during, and after the treatment. One or more temperature sensors or sweat sensors might be placed on the patient body outside of the chamber, such as on a face or a neck of the patient, in order to provide a reference measure of sweat and skin temperature during treatment. In some embodiments, the system comprises a clock to measure the duration of the treatment. In some embodiments, the system further comprises a skin temperature sensor. The skin temperature sensor is placed on the skin of the patient and monitors the skin temperature and verifies that the skin temperature does not, in any circumstance, elevate above 38° C. If the skin temperature elevates above 38° C., the system stops operation of the device.

The system further comprises an anaerobic exercise device disposed in the chamber, the anaerobic exercise device for use by the patient to encourage sweating. The exercise device comprises a pedal exercise device or a spring exercise device for anaerobic exercise that will not elevate the core temperature of the body by more than 0.5° C. The body part comprises one or more legs, one or more arms, a torso, a lower back, or an abdomen. The abdomen comprises up to a chest level and below a heart level. An interior of the chamber is configured such that walls of the chamber are kept spaced from the body part of the subject. In some embodiments, walls of the chamber have direct contact with the body part.

In certain aspects, the invention is directed to methods for treating fluid overload in a subject. The methods comprise shifting fluids directly and non-invasively from an interstitial compartment of the subject to skin of the subject through controlled local fluid loss, thereby removing excess fluid from the interstitial compartment of the subject and treating fluid overload in the subject. In some cases, the fluid loss is sweating. The fluid loss, or sweating, is stimulated by controlling humidity, airflow, pressure, and temperature within a chamber. The methods further comprise calculating a sweat rate within the chamber. The methods further comprise analyzing sweat content and recommending nutritional supplement. In some embodiments, the methods further comprise aerobic or anaerobic exercising of a body part of the subject within the chamber to encourage sweating without increasing the core temperature of the body by more than 0.5° C.

In some embodiments of the invention, the method is carried out using a fluid stimulation system or sweat stimulation system. The fluid stimulation system, or sweat stimulation system, comprises a chamber and first and second relative humidity sensors coupled with temperature sensors. The chamber is sized to fit around a body part of a subject, leaving clear volume of air between the body part and walls of the chamber, comprises an inlet and an outlet, and is configured such that air flows through the chamber from the inlet to the outlet. The first relative humidity sensor is operably located inside the air inlet tubing, and the second relative humidity sensor is operably located proximate the outlet holes. A plurality of sensors provides data to a controller for calculating sweat rate within the chamber. The method further comprises controlling and monitoring conditions of the chamber using the controller, wherein the controller is operable by a user to program conditions of the chamber. The method further comprises monitoring skin temperature of the subject and stopping operation of the system if the skin temperature exceeds 38° C.

Figure 11:
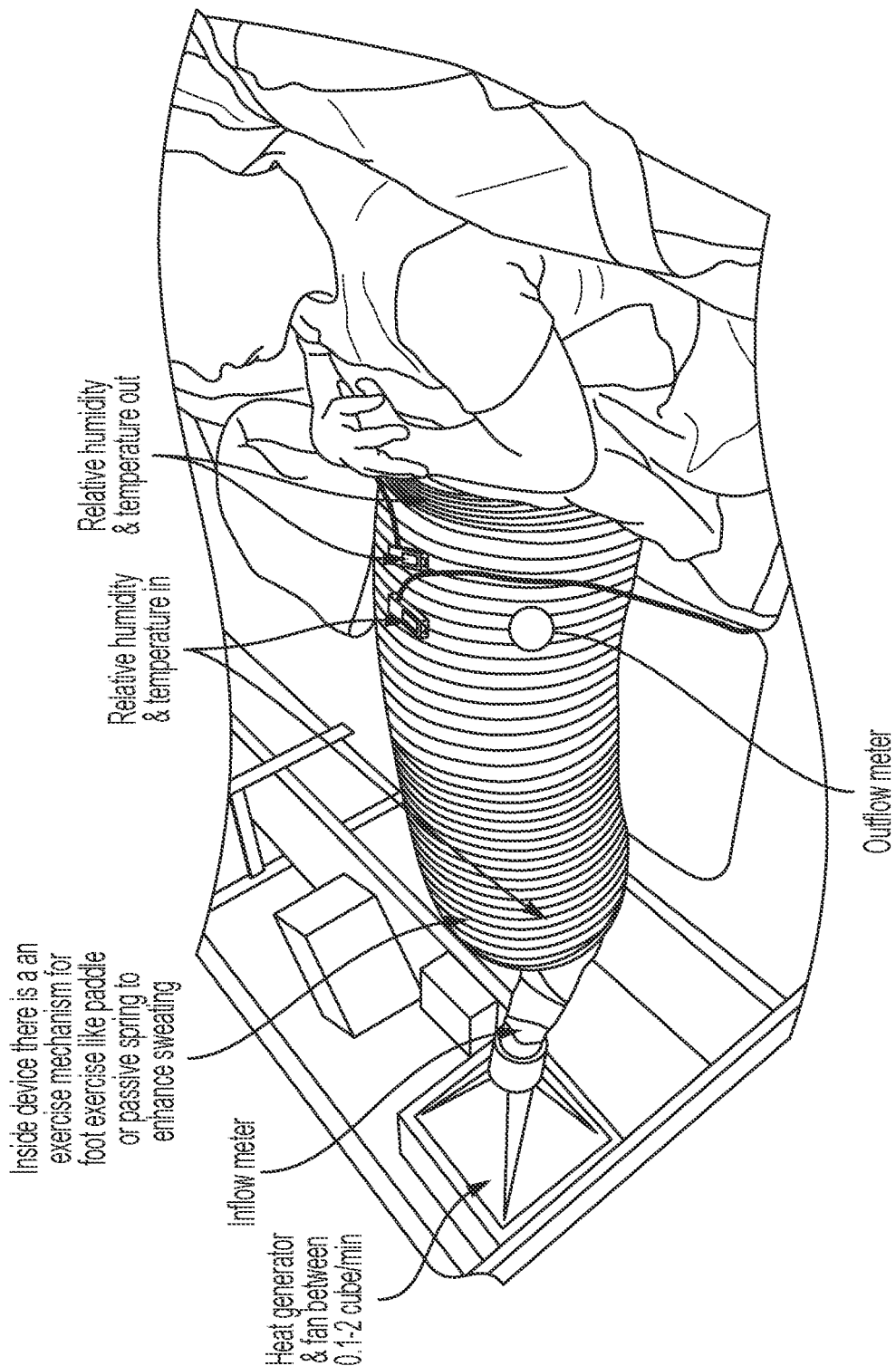
FIG. 11 shows an embodiment of a system of the invention.

FIG. 11 shows an embodiment of a system of the invention. A patient has his legs inserted in a chamber. The patient's legs are fully inserted in the chamber and the chamber end distal from the heat generator and fan is at a lower back or lower chest (torso) level of the patient. A heat generator and fan generate airflow between about 0.1 to about 4 cubic meters per minute. The airflow path travels from the heat generator and fan into one end of the chamber through an inlet at the patient's feet. An inflow meter is disposed at the inlet.

Inside the chamber is a device or mechanism that encourages anaerobic foot exercise (FIG. 13), such as a paddle or passive spring, in order to enhance sweating. Foot exercise performed may be anaerobic and aerobic within the device in order to further enhance sweat rate The chamber is sealed, with at least one inflow and at least one outflow and a combination of humidity sensors at the inflow and outflow to enable calculation of the sweat rate. Airflow travels through the chamber and out and outlet of the chamber. Controllers are communicatively coupled with sensors and measure conditions of the chamber. For example, relative humidity and temperature in are measured at the inlet, and relative humidity and temperature out are measured at the outlet. The system also includes a controller that provides feedback of sweat rate and weight loss.

The invention allows for the skin to stay dry throughout the treatment. This is important because sweat that does not evaporate will slow down any further sweating and will also create an uncomfortable feeling for the patient. Anywhere there is contact between the patient and the chamber, the airflow is reduced and sweat can accumulate, resulting in less efficient sweating. Accumulation of sweat is prevented by keeping the body slightly away from the interior of the chamber. Using a disposable "net" within the chamber or having the patient wear thick clothing are two examples of how to keep the body slightly away from the interior of the chamber, thereby keeping body parts away from direct contact with the chamber. Disposable cloth may also be used to keep the body slightly away from the interior of the chamber, and would provide a benefit during cleaning of the chamber between treatments.

Figure 12:
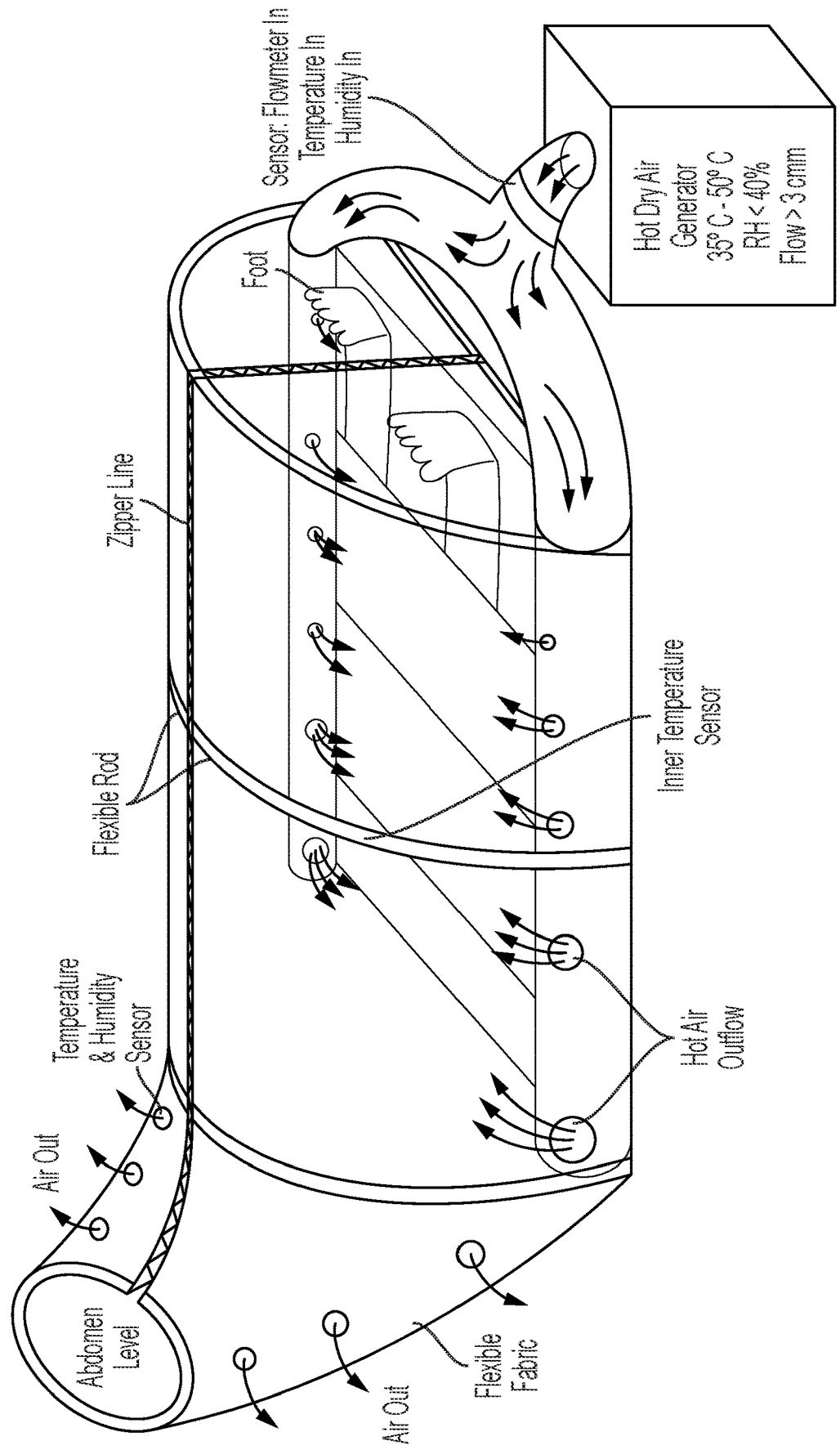
FIG. 12 shows an embodiment of a system of the invention.

FIG. 12 shows an embodiment of a system of the invention. The base mattress is foldable and can be placed on a chair, couch, or a bed. The half circular closing part is based on two foldable quarter circular tent-like structures that, when brought together over the patient's legs and torso, can then be hooked together or zipped to create a sealed chamber insulated against rapid heat loss from its outer surface. The hot air, at a temperature of about 35° C. to about 50° C., enters from tubes at either side of the mattress, is directed inwards, and has various enlarging locations so that the warm air will flow up from its bottom input location. This type of air outflow from bottom to top, with larger holes towards the outflow, provides for uniform temperature of the air inside the chamber. Uniform temperature distribution inside the chamber is important because an optimal temperature for sweating is between about 36° C. and about 39° C. Therefore, keeping the airflow in all parts of the body uniform allows for optimal sweat rates and avoidance of heat damage to the skin. The hot air leaves the sealed chamber at holes created in the flexible fabric part, such as neoprene, around the torso. Typically the patient will decide if to be in bed or couch and then set up the mattress. Next the patient connects the heater to the inlet hose and gets situated on the mattress. The patient brings both quarter circular parts around the body of the patient and zips from the legs up all the way up to the level of the abdomen around the level of the lower ribs to create a chamber.

Figure 13:
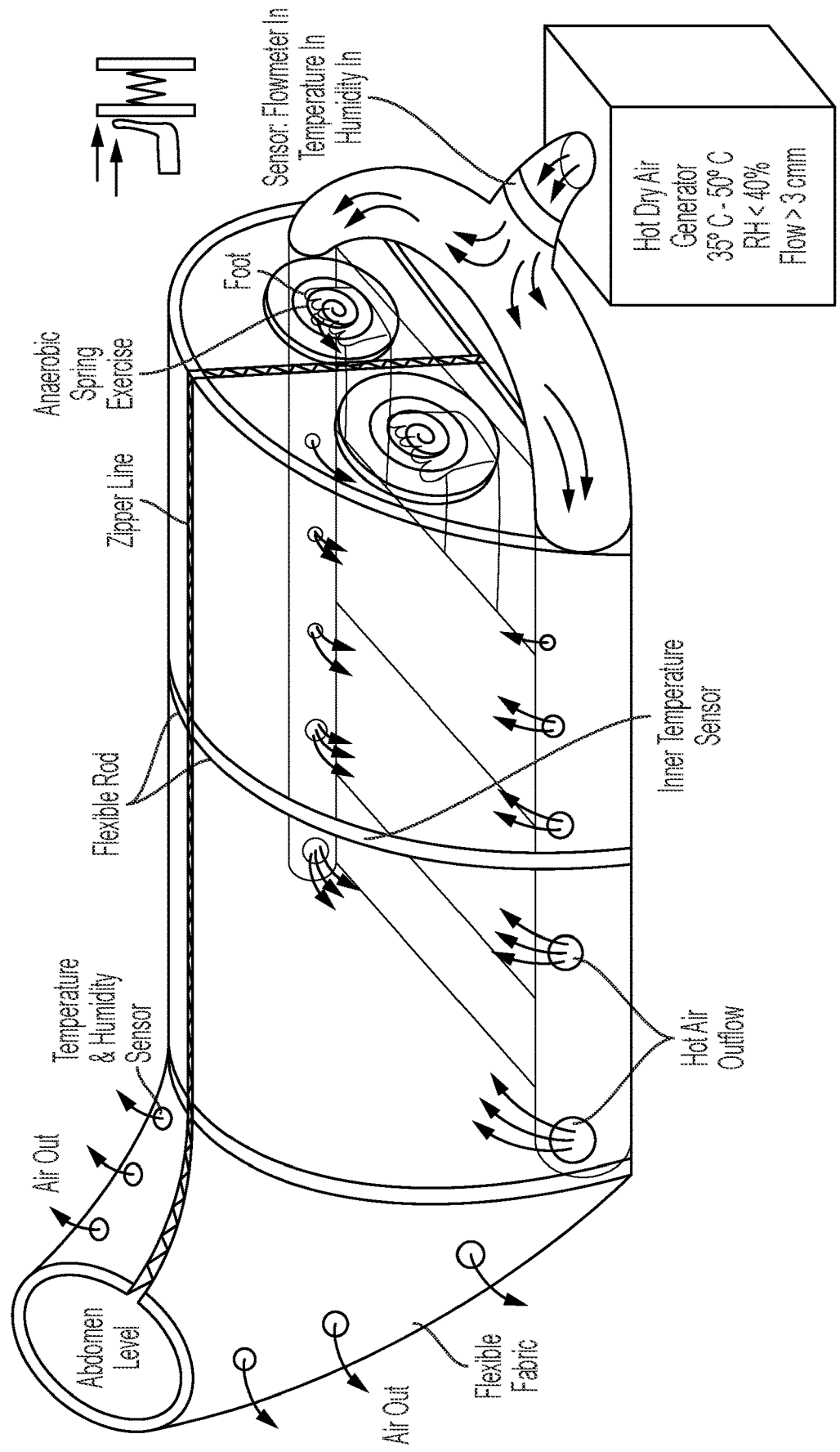
FIG. 13 shows an embodiment of a system of the invention.

FIG. 13 shows a foot exercise device. An anaerobic spring exercise device is shown in the chamber for use by the patient. The patient uses his or her feet to operate the anaerobic spring exercise device, thereby encouraging sweating.

Figure 14:
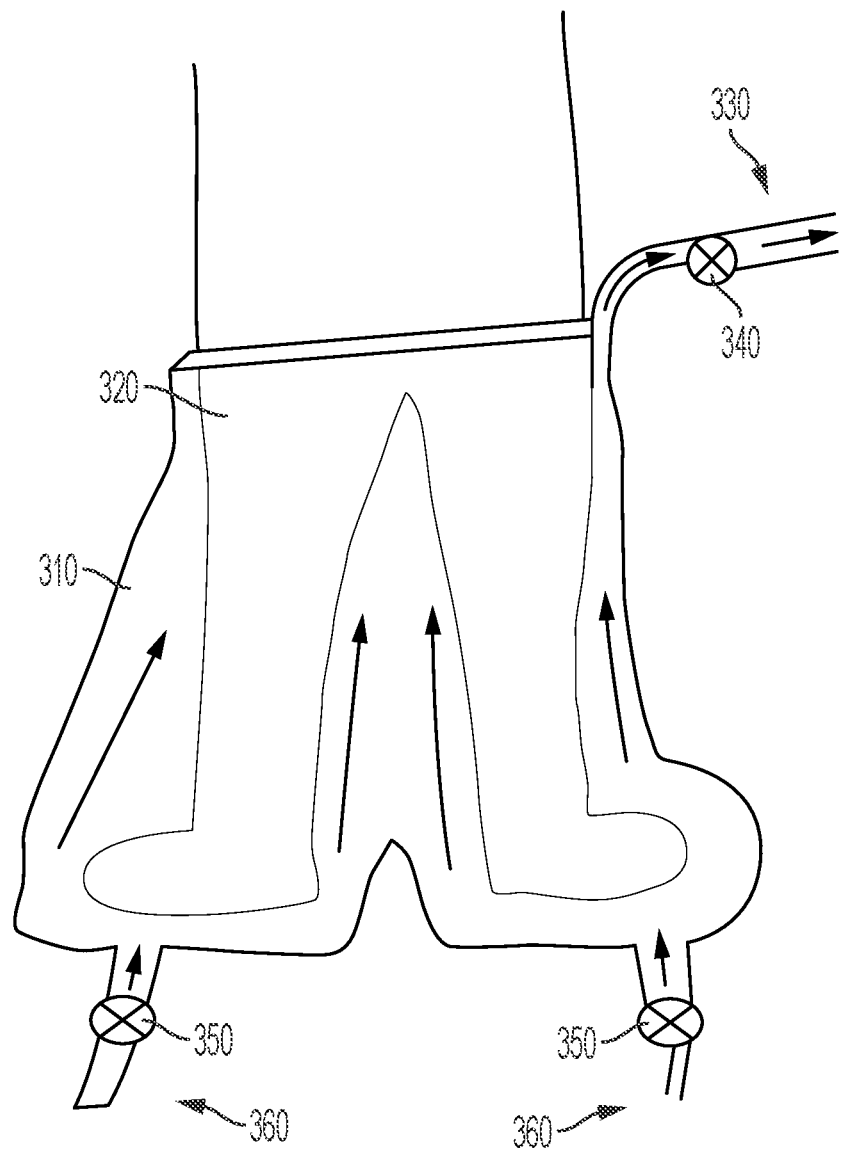
FIG. 14 shows an embodiment of a system of the invention.

FIG. 14 shows an embodiment of a system of the invention. A warm air cuff 310 is fitted around the legs 320 of a patient. The cuff 310 has one or more hot air inlets 360 and one or more outlets 330. A relative humidity sensor 350 is disposed at the hot air inlet 360. Dry warm air at a temperature of about 32° C. to about 45° C. at a relative low humidity of less than about 85% is fanned into the warm air cuff 310 at the hot air inlet 360. The relative low humidity may, for example, be about 85%, 80%, 75%, 70%, 65%, 60%, 55%, 50%, 45%, 40%, 35%, 30%, 25%, 20%, 15%, 10%, or 5%. Air and sweat are exhausted from the cuff 310 at the outlet 330. A second relative humidity sensor 340 is disposed at the outlet 330.

In some embodiments, the chamber is sized to fit around a patient's abdomen, one or two legs, one or two arms, a back, or any combination thereof. In some instances, the chamber may cover a substantial portion of the patient's body below the chest, for example, covering around 1 square meter of surface area and providing fluid loss at a rate of approximately 200 ml/hr.

The patient can request, or be prescribed, a certain amount of sweat per treatment. The systems of the invention will calculate sweat rate, display, and stop the operation of the system once the desired sweat amount is obtained. Calculation can be performed using input from the two humidity sensors and their difference in readings over time, such as every few minutes.

In another embodiment, the invention is directed to removing fluids from the body in order to maintain intravascular fluid balance by driving fluids through the skin by osmosis, either alone or in combination with sweat production. A cuff with high concentration of intravascular large molecules can be tight around the body legs arms or abdominal cavities and through a semipermeable cuff water or dry air will start to flow out through the skin and into the cuff. This way, fluids can shift out of the body and fluid balance can be maintained. This method can be done by the patient at home and eliminate episodes of severe fluid overload.

Figure 15:
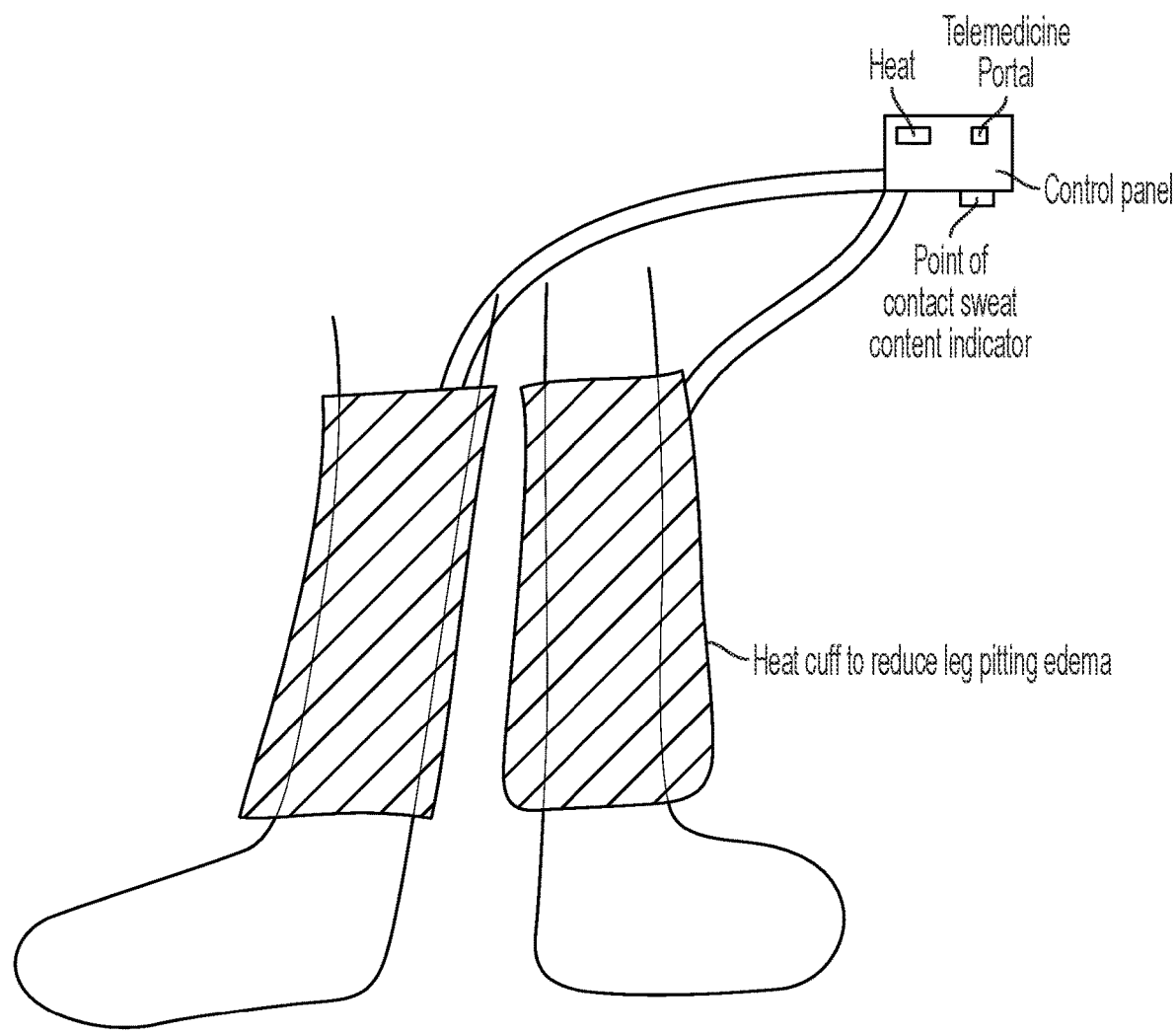
FIG. 15 shows an embodiment of a system of the invention.

FIG. 15 shows an embodiment of a system according to the invention. Heat cuffs are fitted around legs of a patient to reduce leg pitting edema. A control panel is communicatively coupled to the heat cuff. The control panel includes a heat indicator and point of contact sweat content indicator. The control panel is capable of communicating with a telemedicine portal to program and monitor the treatment.

In some embodiments, the invention is directed to a method of removing fluids through the skin by osmosis. The method comprises fitting a chamber around a body part of a patient, the chamber comprising interstitial electrolytes. The method further comprises controlling content and concentration of the interstitial electrolytes in the chamber, thereby driving water and salts out of the body part of the patient while maintaining pH and electrolyte levels of the body part.

Figure 16:
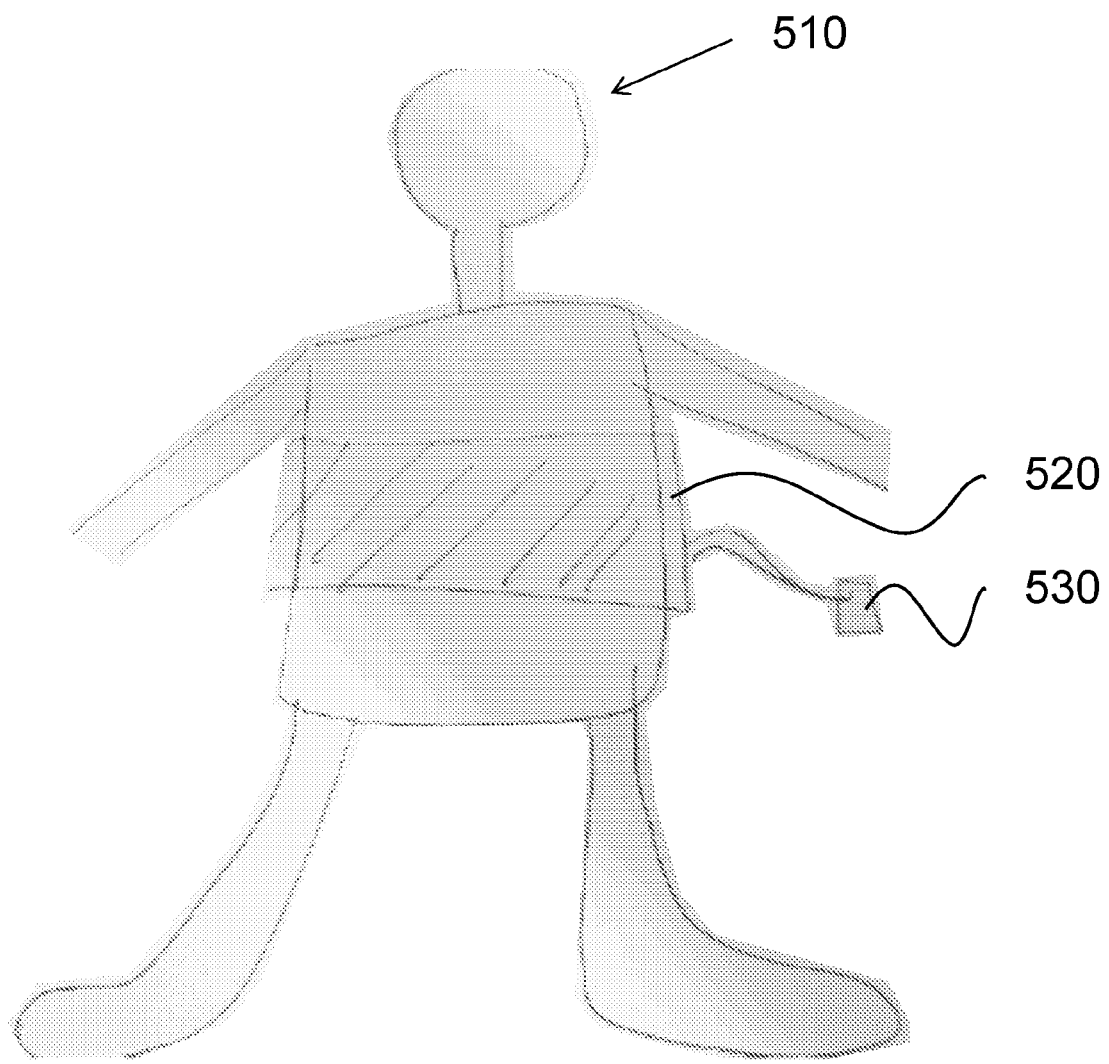
FIG. 16 shows an embodiment of a system of the invention.

FIG. 16 shows an embodiment of a system according to the invention. A patient or subject 510 has a cuff 520 fitted around the patient's abdomen. A control panel or controller 530 is communicatively coupled to the cuff 510. The controller allows for communication with a telemedicine portal or network and the controller may comprise a plurality of sensors for monitoring of conditions of the cuff, such as temperature, sweat content, and humidity.

The cuff 520 may provide a wet environment with specific, controlled mineral content. For example, the mineral content is primarily salts and electrolytes, such as sodium potassium and chloride. In such a scenario, creation of an osmotic pressure favoring outflow of fluids from the body, not through sweat glands, is applied. The mineral content drives fluids out of the body by the mechanism of osmosis and also balances the electrolytes and mineral composition of the fluids as required in the body.

In some embodiments of the invention, fluid loss may comprise saliva generation. The saliva glands can produce up to about 2.5 liters of fluid per day. Stimulation of saliva glands can be achieved by chewing gum or any other material suitable as a stimulator. The saliva can be collected, measured, and analyzed. The system might have a flavor, such as a flavored mouthpiece, that will stimulate production of saliva.

In certain embodiments, the invention is directed to a fluid loss stimulation device comprising a housing. The housing comprises a mouthpiece, a storage chamber, and suction. The mouthpiece is disposed at a proximal end of the housing. The device comprises a power button for providing power to the suction. For example, battery power may be used to power the suction, which may be any suitable suction component, such as a pump. The suction is configured to deposit saliva from a mouth of a patient into the storage chamber of the device. The storage chamber is removably detachable from the device. For example, the storage chamber may comprise a threaded end that is couples with threads on a body of the device. Rotation of the storage chamber results in detachment of the threaded components.

Figure 17:
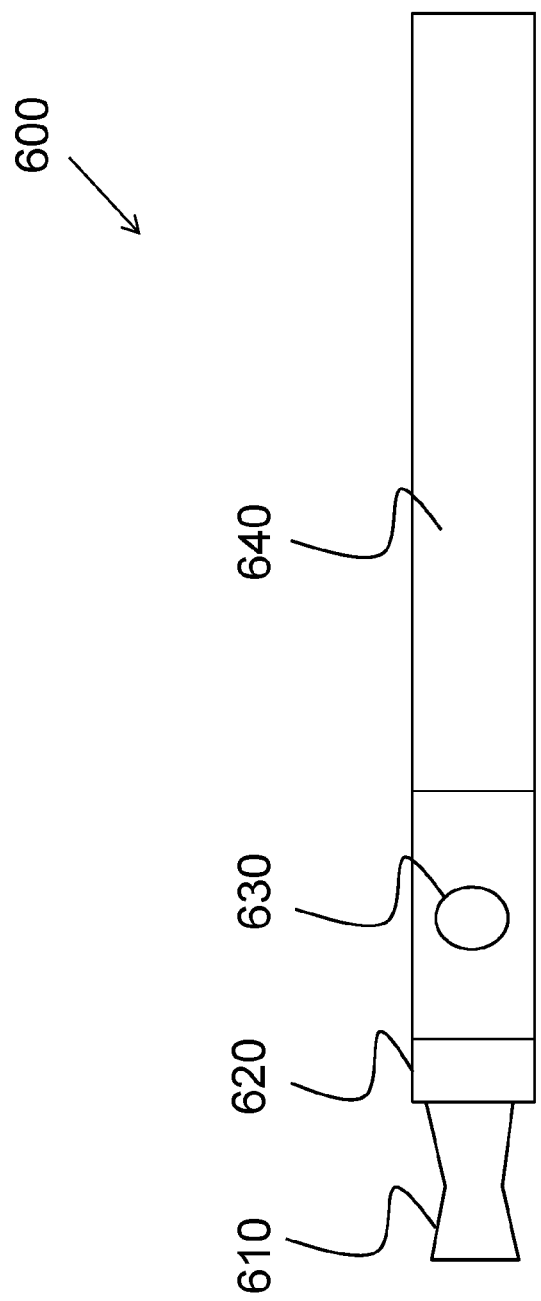
FIG. 17 shows an embodiment of a system of the invention.

FIG. 17 shows a device for saliva production. The mouthpiece 610 of the device 600 is inserted into a mouth of a patient or subject. A suction component 620 is provided distal to the mouthpiece 610. The device 600 includes a power button 630 that provides power to the suction component 620, allowing for suction of saliva from the patient's mouth into the device. The saliva may be stored in a chamber 640, operably removable from the device 600 in order to empty the stored saliva. Optionally, the patient may chew gum in order to stimulate fluid production during treatment.

The invention also recognizes that as sweat leaves the body through skin, a portion of sodium from the sweat is re-absorbed back into the body to maintain a proper salt balance. Without being limited by any particular theory or mechanism of action, it is believed that in certain instances, the induction of sweating can lead to a salt imbalance since water is rapidly lost while sodium is re-absorbed back into the body. In certain embodiments, if such imbalance does occur and needed to be addressed, other methods and systems of the invention include introducing negative ions into an airflow that contacts a surface of skin at a site where sweating is induced. Since sodium is positively charged, once sweat leaves the body in the presence of the negative ions, attractive forces between the positively charged sodium atoms and the negatively charged ions prevent sodium being re-absorbed back into the body, thereby preventing a salt imbalance.

Such methods and systems of the invention may include introducing anions to a surface of a patient's skin at a site where sweating is induced. Anions may include any atomic or polyatomic ion with a negative charge. For example, the anions introduced by systems of the invention may comprise any one of carbonate, sulphate, bromide, chloride, fluoride, iodide, nitride, oxide, or sulfide ions, or any combination thereof.

Methods and systems of the invention include adding negative ions to air that flows through a chamber dimensioned for fitting around a body part to stimulate sweating. Negative ions can be put into the airflow by any number of methods capable of introducing ions into air in advance of the air contacting skin at the site of induced sweating. For example, in some embodiments, negative ions may be introduced into the airflow by an ion-exchange resin or ion-exchange polymer. An ion resin is a resin or polymer that functions as a medium for ion exchange and is generally in the form of porous microbeads. The ion resin may be either strongly or weakly basic. In certain instances, methods and systems of the invention include placing the ion resin at an inlet of the chamber such that as air flows through the inlet, the air passes through the ion resin to incorporate negative ions into the airflow. Ion resins can be purchased commercially or may be synthesized, for example, as described in Japanese Patent Application JP2002302665A, incorporated by reference.

In other embodiments, negative ions may be introduced into an airflow that passes through a chamber by placing a negative ion generator at an inlet of the chamber. Negative ion generators considered by the invention include any device capable of supplying negative ions to air, for example, such as those described in U.S. Pat. Nos. 3,403,252A, 3,504,227A, 9,071,040, each of which are incorporated by reference. For example, salt can be dissolved in water. The water and the salts are then sprayed into the air inflow line. Once in the air inflow line the humid air now containing sodium and chloride anions passes through a resin that catches sodium ions. Flowing into a fluid stimulation system worn around a patient's body are negatively charged ions at a relatively high humidity (50%-75%). Providing anions at a relatively high humidity, capable to still evaporate sweat, will attract the sodium ions inside the body to the skin and increase the sodium sweat concentration.

In certain aspects, methods and systems of the invention provide a fluid stimulation system with a chamber sized to fit around a body part of a subject to stimulate fluid loss. The chamber sized to leave a clear volume of air between the body part and walls of the chamber. The chamber includes an inlet and an outlet and is configured such that an air flow passes through the chamber from the inlet to the outlet. The air flow may include negative ions introduced by a component of the system. For example, one of bromide, chloride, fluoride, iodide, nitride, oxide, or sulfide ions may be introduced into the airflow. In certain instances, the component is an ion resin located near the inlet of the chamber. Alternatively, the component may be a negative ion generator located at an inlet of the chamber.

In other aspects, the invention provides methods for treating fluid overload in a subject. Methods include shifting fluids directly and non-invasively from an interstitial compartment of the subject to skin of the subject through controlled local fluid loss, thereby removing excess fluid from the interstitial compartment of the subject and treating fluid overload in the subject. Methods further include introducing negative ions into the airflow to inhibit sodium re-absorption during fluid loss.

In some aspects, methods and systems of the invention provide a fluid removal treatment device that patients can use on the go or from the comfort of their home. Some embodiments provide a portable device that can be worn for a few hours or may be worn overnight to eliminate excess interstitial fluid by sweating. The device may comprise an apparatus such as a cuff, chamber, or sleeve that creates a controlled environment around a body part, such as, an arm, leg, abdomen, back, or a combination thereof. In some instances, the device can reduce afterload by heating and increasing cutaneous vascular conductance. As such, patients may find using the device overnight is useful for treating dyspnea and/or orthopnea to improve sleep.

In some embodiments, the invention provides a mobile apparatus such as a cuff, chamber, or sleeve that a patient can wear around a body part to stimulate fluid loss while the patient is moving around. The apparatus may be designed to allow freedom of movement so that the patient wearing the apparatus can, for example, cycle or jog in it. In particular, the apparatus may be useful for improving exercise tolerance by reducing breathlessness. In some instances, the apparatus is sized for wearing underneath the person's clothes so that it is less apparent.

Methods and Devices to Remove Extracellular Fluid Overload (Edema) Via the Skin

Extracellular Fluid Overload (Edema) is a medical condition in which excessive fluid accumulation in the intravascular and/or interstitial compartments occur. If left untreated tissue function as well as gas exchange can be compromised leading to hospitalization.

The causes of the edema can be of many etiologies some of which are elevated intravascular hydrostatic pressures, changes in either intravascular or interstitial osmotic pressure, lymphedema, hypertension and obesity.

Accordingly, the invention recognizes that methods and devices that reduce edema whilst the patient is still in a chronic state and not acutely hospitalized could be very beneficial.

In some aspects, this disclosure provides systems and methods for stimulating fluid transfer through the skin in a subject for treating chronic edematous clinical conditions in the subject and before they become acute heart failure episodes.

For example, fluid from the extracellular compartment can be removed directly from the skin by either sweat production in the sweat glands or via the dermis by means of osmosis.

It is generally accepted that fluid removal rates ranging from 50 ml/hr-300 ml/hr can enable prevention of excessive edema that if left untreated can lead to acute decompensation and hospitalization.

Fluid can flow out of the skin through the sweat glands at a rate of liters per hour if the sweat glands are stimulated in the most aggressive way. However, may not be tolerated by patients and may result in a hemodynamic shock.

Therefore, a method and device that fits the patient fluid status is provided herein.

The method may locally elevate a temperature of a patient's skin to values from 35° c. to 38.5° c. by applying warm (38° c.-44° c.) and low humidity (less than 40%) air environment around the patient's lower half of the body for durations of 1 hr-6 hr. The timing may depend on factors such as edema severity. Such a method may achieve a fluid removal rate of between 100 ml/hr-300 ml/hr.

Air may be supplied by a generator console which has control of air temperature, flow rate, humidity and additional parameters which assure safe and effective operation. The lower part of the body is the preferred area of treatment as it will be better tolerated by the patient; however, the invention recognizes that other parts of the body may be treated, such as, the hands, chest, or back, especially if those other parts are edematous.

Partial body skin temperature elevation to values between 35° c. and 38.5° c. are expected to maintain core body temperature at normal values elevating no more than 0.5° c. at maximum and initiate sweat at a rate that between 100 ml/hr-300 ml/hr when the part of the body that its skin pressure is elevated is the lower prat of the body from the abdomen and lower back down to the feet.

In some respects, part of the method may relate to treating a patient either outside the hospital, i.e., in his home environment, or in the outpatient clinics, so as to prevent acute medical conditions or hospitalization.

For the patient to tolerate daily or weekly 1-6 hr treatments, it is desirable that the device enables the treated patient to be mobile whilst being treated. Therefore, the console unit preferably enables elevation of the skin temperature to values between 35° c. and 38.5° c. while the patient can be mobile. As such, the patient may be mobile whilst being treated. A specific apparatus may be worn by the patient, along with a specific heat generator, to enable mobility.

In some respects, this disclosure provides a uniquely designed wearable (dress) "capsule" and a mobile console. The wearable capsule may be loose around the lower part of the body or any part of the body in which movement of fluids from the extracellular compartment out of the body via the skin are required. The capsule may be made from soft fabrics, for example, Neoprene, that are tightened around the lower ribs to prevent warn air from blowing towards the upper parts of the body or the face, or ridged material for example shell made of metal or polymers. At a portion near the feet from a tightened belt the capsule may keep a distance of between 2 cm-10 cm from the skin when air flow is directed to the volume between the skin and the capsule wall.

When lying down, the capsule may be closed at the level of the feet to enable preservation of the warm air also at the flat position.

When standing or walking, the capsule may be opened at the level of the feet to enable free movement of the body.

The capsule may include a console. The console may be a light weight, rechargeable, mobile stand which is connected to the wearable capsule by a tube at a distance of 0.5-2.0 meter. This tube delivers the air and the electrical communication of the sensors are used to control the operation of the system and the body parameters of the body.

When keeping the capsule loose from the body yet up to 10 cm away, the trapped air volume can be between 0.2 cubic meter-0.5 cubic meter. This air volume can be heated from ambient temperature ranging from 17° c. to 30° c. to, for example, a required temperature range of 38° c. to 45° c.

The required temperature range may cause the skin temperature to be elevated to the required range of 35° c. and 38.5° c. The requirement to preserve low humidity, for example, less than 50% also when the sweat rate is 300 ml/hr, may be crucial for the patient's treatment so that sweat will not accumulate on the surface of the skin and will evaporate. If the sweat will not evaporate then the sweat rate will decrease and the patient discomfort may lead to patient noncompliance.

At such a sweat rate and a base surrounding humidity of around 30% at 40° c. the air flow through the capsule needs to be at least 0.2 cubic meter per minute (cm/m) and preferably 0.3 cubic meter or more per minute (cm/m).

Taking at least some, and preferably all, these unique requirements will enable a mobile and effective treatment. Preferably, the design of the capsule and its connection to a console based heater will include the following specifications:

1. Power requirement: 80 watt-250 watt
2. 8 Amps-20 Amps
3. 12 VDC-48 VDC These top 3 requirements will enable temperature increase of around 20° c. at a heating rate of 1 minute
4. Air flow blower: up to 0.7 cmm
5. Capsule worn the chest (lower ribs) down to the feet, or as required to treat other parts of the body
6. At the upper level of the capsule a belt will be tightened to ensure that air does not flow towards the upper levels of the body
7. The capsule has an option to be sealed at the level of the feet when the patient prefers to be treated when seating down or laying down
8. The warm air enters that capsule at the level of the knees
9. The heater is mounted on a pole that can be carried around the house during the treatments
10. The system can be operated and controlled via app. Installed on a smart phone of the user. The smart phone connected to the system by a slot in the console, allowing data recording, control and sharing of the data.

Figure 18:
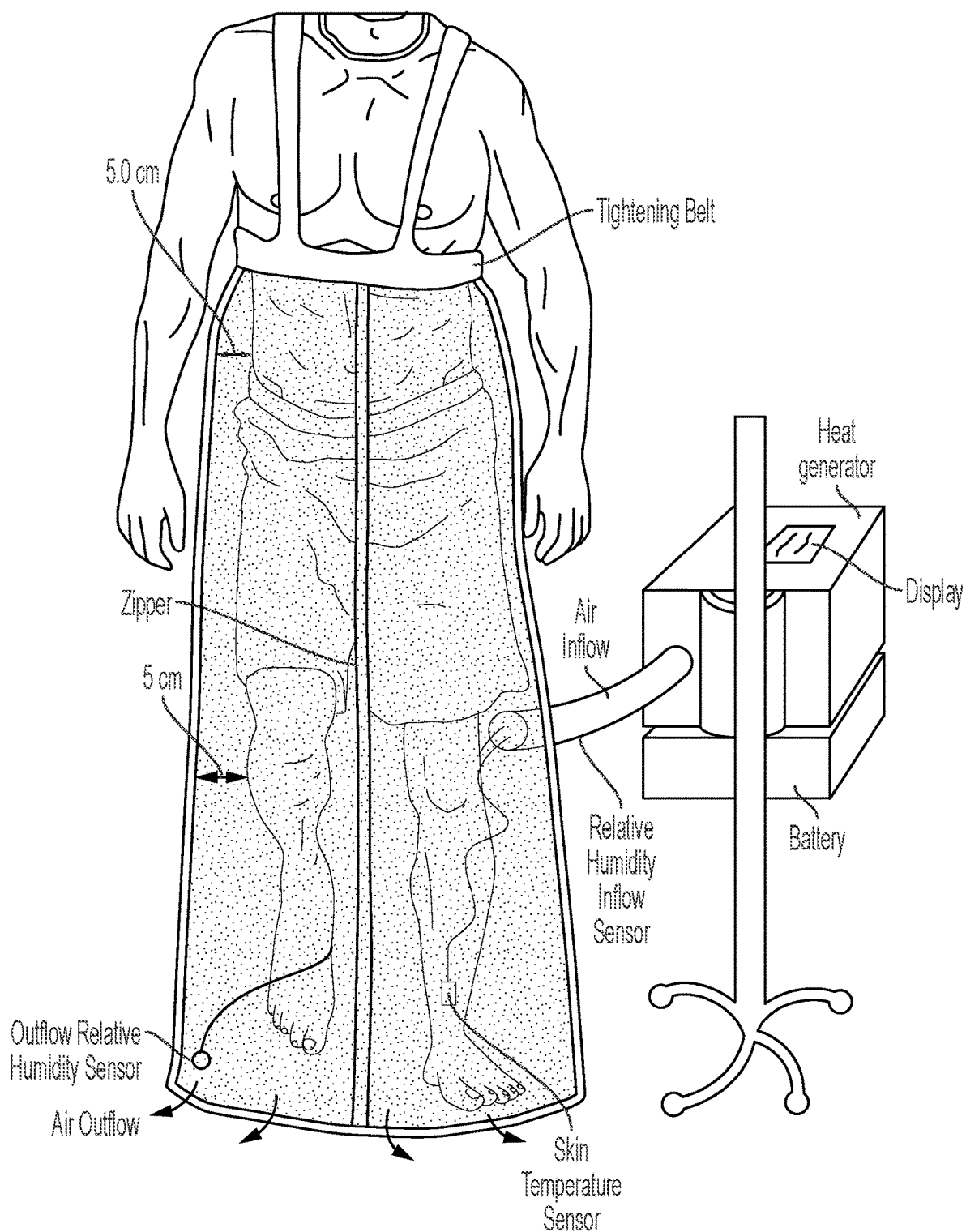
FIG. 18 shows an example configuration of a device of the invention.

FIG. 18 shows an example configuration of a device of the invention. The heater unit may have any one or more of the following features:

1. Relative humidity of air inlet.
2. Relative humidity of air outflow from a humidity sensor at a bottom of the capsule at the air outlet.
3. Temperature of capsule.
4. Temperature of skin on the calf as measured by a skin temperature sensor.
5. Preset alarm and system shut down when skin temperature is above 38.5° c. or capsule ambient temperature above 44° c.
6. Air flow rate.
7. Calculated sweat rate from the difference from inlet to outlet absolute humidity multiplied by air flow rate.
8. Wireless sending of information to the physician status.

Accordingly, in some respects, this disclosure provides methods and devices to reduce edema by enhancing fluid transfer through the skin. This disclosure may provide a mobile system, comprised of a wearable and a console, to elevate skin temperature to initiate sweat production. For example, a wearable device to create a warm air environment at a predetermined volume around the body to initiate sweat production and reduction of edema. Methods and devices may be controlled by smartphone application.

Method and Apparatus to Treat Orthopnea and Paroxysmal Dyspnea (PND)

Orthopnea and PND are medical conditions in which patients feel that they cannot breathe freely in the supine or recumbent positions. Unless their head is elevated, or their upper body is inclined, they cannot sleep at night or they wake up frequently feeling shortness of breath.

The supine or recumbent positions are important for maintaining hemostasis due to the diuretic effect in these positions. Therefore, and apart from the discomfort of not being able to sleep in supine, these patients do not produce urine output at a rate that they would have if they were laying supine.

Many Patients that suffer from Orthopnea and PND suffer also from Edema because of heart failure or Lymphedema. Treating or relieving the Orthopnea and PND can improve their ability to lay supine and maximize their diuresis during the night.

One of the main causes of Orthopnea is the pressure exerted by the abdomen on the diaphragm and the elevated pulmonary vasculature pressures in the supine position. Both these causes either interfere with alveoli gas exchange or stimulate the receptors responsible for the shortness of breath feeling.

Therefore, an apparatus that will reduce the blood pressures or the abdomen pressure on the diaphragm can improve the shortness of breath, enable supine position with the enhanced diuresis and improve edema status.

Systems and methods of the invention recognize that there are at least two separate apparatus features that may independently improve and may reduce the pressures in the thoracic cavity:
1. Enabling vasodilation of the blood vessels to reduce blood pressures and improve shortness of breath; and
2. Holding the abdomen from pushing on the diaphragm in the supine position will enable the stretching of the diaphragm in the supine position and reduction of pressure An apparatus that can perform both features is novel and can improve the medical status of these patients.

Accordingly, in some respects, this disclosure provides an apparatus that enables the following features:

A. Enabling Vasodilation of the Blood Vessels to Reduce Blood Pressures and Improve Shortness of Breath.

The apparatus covers the lower part of the body from the chest down to the feet. The apparatus can be made from fabrics that are loose around the lower part of the body and tightened no the lower chest or abdomen. A warm air generator may produce temperatures between 37 and 45 degrees Celsius and at flow above 0.5 meter cube per minute. The war air generator may be connected to the apparatus and generate warm air environment surrounding the lower part of the body at controlled temperatures. This warm air surrounding may create conditions which the vasculature, especially around the skin, is vasodilated.

The vasodilation may be controlled by the hypothalamus and the cutaneous vascular conductance receptors to thermoregulate the core body temperature. In addition to the initiation of sweating and its evaporation, the body ensures that the core body temperature remains within a normal range.

The apparatus may ensure that the skin temperature is below 40 degrees Celsius by monitoring the skin temperature at the toe, or at any other location in which the skin temperature is high, and whenever the reading is above 39 degrees Celsius, the warm air generator may stop to function until the temperature drops down to 38 degrees Celsius.

Furthermore, the apparatus may use warn air generator at relative humidity below 50% to ensure that if sweating occurs it will evaporate and will not cause discomfort to the patient.

B. Holding the Abdomen from Pushing on the Diaphragm in the Supine Position

The upper part of the apparatus is tightened around the lower part of the chest and specifically around the lowest ribs and push the abdomen towards the pelvis and away from the diaphragm.

In the supine position this will enable full inspiration movement of the diaphragm with the accompanying low inspiration pressures. The apparatus may employ any number of fastening mechanisms, such as, Velcro and/or a zipper, to ensure that it does not slip down from its optimal position.

Figure 19:
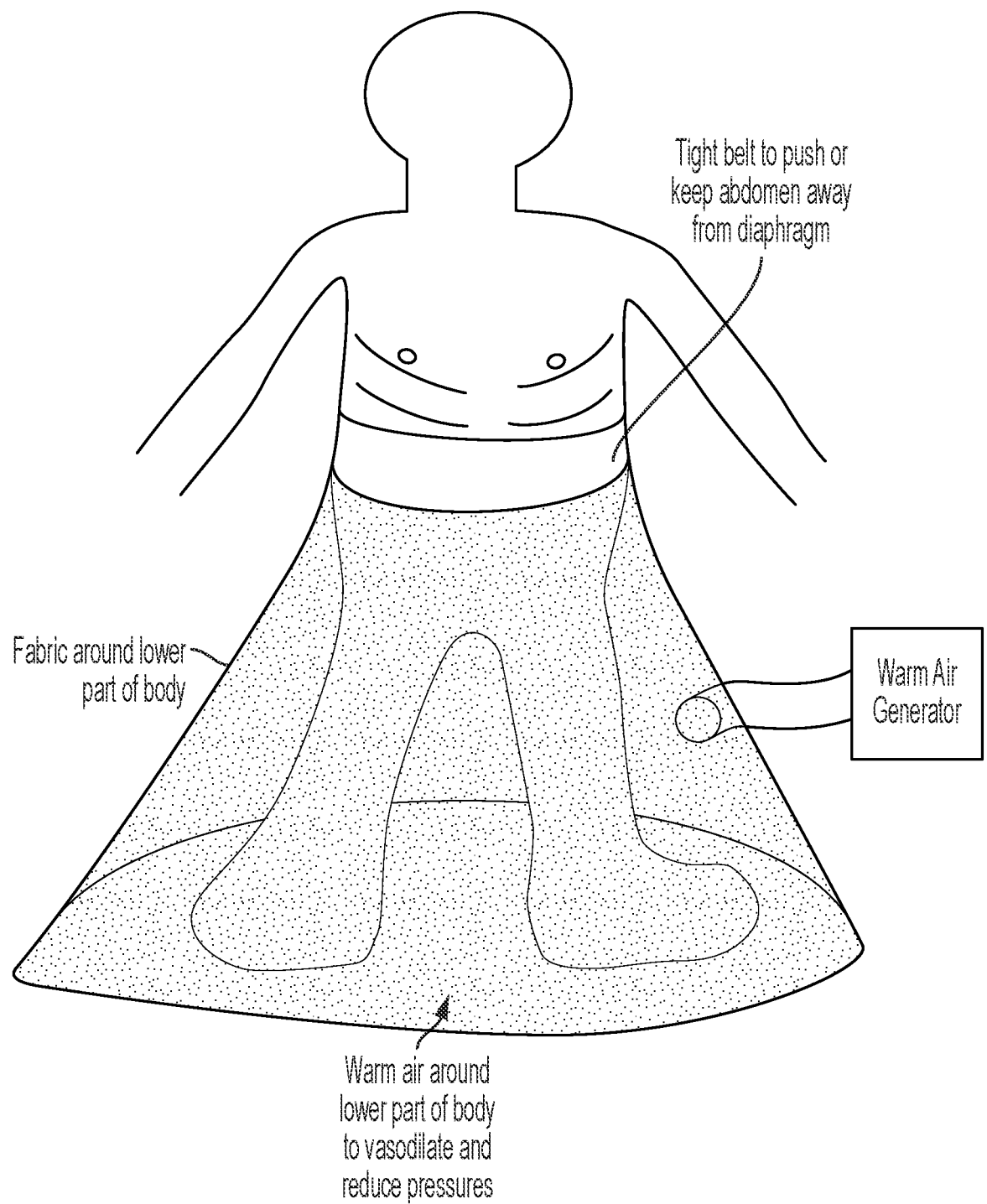
FIG. 19 shows an exemplary apparatus of the invention.

FIG. 19 shows an exemplary apparatus of the invention. The apparatus includes a tight belt/Velcro at the lower chest level to push abdomen don towards the pelvis and to disable warm air flow towards the face. And, an arm air generator assembled to a loose fabric "capsule" elevating skin temperature, causing vasodilation, and reduction of Orthopnea.

Accordingly, in some aspects, this disclosure provides, a method to reduce Orthopnea and PND shortness of breath and enable supine position sleeping and/or enhanced diuresis when laying down. The method may reduces blood pressure and enables diaphragm full inspiration stretching. An apparatus that increases the temperature at a part of the body and as a result creates vasodilation of the vasculature, reduce pressures and improved shortness of breath feeling. An apparatus that pushes the abdomen away from the diaphragm by actively pressing or pulling the abdomen towards the pelvis.

Methods and Apparatus to Control Extracellular Electrolytes and Fluid Balance Via the Skin Extracellular electrolytes balance, especially sodium and potassium concentrations in the interstitial compartment are important to preserve hemostasis and prevent water retention. Ways to control the electrolyte concentration may include food and fluids intake or by drugs that work on the kidneys to either dispose of or preserve electrolyte concentration.

In many pathologies, such as chronic kidney dysfunction (CKD) or heart failure (HF) there is an electrolyte and fluid imbalance that leads to hospitalization or chronic need for dialysis.

Switching to another biological system, sweat glands secrete fluids from the interstitial compartment. The fluids that enter the secretory coil part of the sweat gland is isotonic to plasma with Na+ concentrations of around 140 mmol/liter.

Once sweat flows towards the skin surface part of the sodium gets reabsorbed by the Apical and Basolateral membranes of the sweat duct according to the leak-pump model. Because of the reabsorption the Na+ concentration on the skin is hypotonic and can range, depending on the sweat rate between 10 mmol/Liter-100 mmol/Liter. Controlling the sweat sodium concentration can have a great effect on the fluid status of a patient with CKD or HF and potentially prevent them from being fluid overloaded.

The plasma Na+ concentration is strictly controlled between a small range of less than 10 mmol/Liter and therefore alterations from this range to either hypo or hypernatremia can have grave consequences.

In some aspects, this disclosure relates to methods and systems for controlling fluid and electrolytes such as sodium, potassium and chloride concentration by controlling their transfer through the skin during sweat.

Applying a warm air environment around a part of the body may initiate sweat when the skin temperature elevates above 33 degrees Celsius. To ensure that the skin does not start to burn, the temperature of the skin is preferably always be kept below 39 degrees Celsius.

Methods disclosed herein may control the reabsorption rate of the sodium ions at the duct by attracting them to the skin surface using a negatively charged ion at specific relative humidity environment produced by the apparatus on the skin surface or in the air surrounding the skin.

For example, if surrounding the skin, whilst sweating is stimulated, would be a negatively charged carbonate CO3 or OH anion, the sodium cations in the duct may enhance the flow towards the skin rather than being diffusing into the apical membrane. The reabsorption rate of the sodium into the interstitial compartment of the skin will be reduced and the sodium concertation will not elevate. This clinically could be very meaningful as the electrolytes, especially the sodium, determines edema status by binding to fluids.

In some aspects, this disclosure provides a combination of stimulating sweat production and controlling the electrolytes reabsorption rate, thus increasing or decreasing the extravascular sodium and potassium or any other electrolyte concentration.

One example of an apparatus of the invention includes a single, or multiple use, 2 stage apparatus that is placed in the air inflow line of a warm air generator to increase the skin temperature to initiate sweating.

In the first stage of the apparatus, a soluble salt such as K2CO3 may be dispersed into the inflow of air at a temperature of, for example, 40 degrees Celsius-46 degrees Celsius and at a relative humidity of between 30%-50%.

The salt may be soluble and may naturally separate into cations and anions.

In the second part of the apparatus, the air with the K2+ CO3− ions may be passed through a cation resin filter beads that filter the cations and only allow for the anion in the air (H+ and K2+) to flow onto the skin inside the apparatus.

The air, being negatively charged, may increase sodium attraction to the skin surface from the ion bonding attraction and as a result, decrease the reabsorption rate of the sodium. Preferably, the sodium concentration in the interstitial compartment will decrease in addition with plasma sodium levels.

Another apparatus may be a filter. The filter may be placed online to the air inflow line in which all the current electrolytes in the air are filtered. An environment of humidity of around 50% may be created by passing the air into a hydrated environment. As a result, the capacity of the air to attract the sodium cations may increase as they will bind to the negative ions of the humid air water molecules.

Other methods for attracting the sodium molecules to the skin surface may involve using a negative hydrostatic pressure environment whilst stimulating sweat. The negative hydrostatic pressure may enhance sweat flow to the skin and increase the sodium concentration on the skin and reduce its interstitial concentration.

An exemplary apparatus may be a permeable container loaded into the inflow of the air and having K2CO3 salt that has a solubility in moist air that is very high. Once partially dissolved, CO3 anions will then attract the Na+ electrolytes from the sweat duct and will reduce their reabsorption.

Accordingly, in some aspects, this disclosure relates to a method to reduce sodium concentrations in the plasma and interstitial compartment by enhancing sweat rate and pulling to the skin surface the sodium cations using air having negatively charged anions.

Furthermore, this disclosure may provide an apparatus for enhancing sweat using warm air generated into a wearable around the body elevating the skin temperature to levels of between 33-39 degrees Celsius. Furthermore, in the warm humid air inline pipe there is a 2 stage disposable apparatus: The first stage is a disperser a soluble salt into the humid air. As the air flows through the disperser the air becomes full with ions. The next stage is to pass the ion filled air through a cation resin filter. The warm air that will exit the filter and flow around the skin will be negatively charged at huminites around 50%. This air when flowing around the sweating skin will pull the sodium ions to the skin surface and reduce its reabsorption Methods and Apparatus to Control Extracellular Electrolytes and Fluid Balance Via the Skin Patients with heart failure suffer from frequent fluid overload in the interstitial and intravascular compartments as a result of elevated hydrostatic or osmotic or both these pressures within the capillaries. The elevated pressures lead to fluid overload formation. This is a serious medical condition and can become a life-threatening.

Current therapies mostly rely on drugs that reduce intravascular volume and pressure by enhancing urine production. These therapies require complicated sequence of clinical events and often lead to kidney dysfunction, drug resistance and inefficient treatments. New therapies are highly required to meet this great unmet clinical need that millions of patients suffer from.

The fluids in the interstitial compartment supply the sweat fluids to the eccrine glands and therefore can be secreted out of the body through a natural pathway of these glands through the skin. This natural pathway can be used to decongest fluid overload and treat HF patients. In order to efficiently decongest these patients suffering from fluid overload through the skin a sweat rate of between 100 ml/hr-500 ml/hr is recommended. Lower rates may not be efficient and too high rates can be dangerous and lead to hypotension.

It is highly recommended to have an option to treat the patients also at home and therefore a controlled and automated system that will decongest the patient's fluid overload without the requirement of in-hospital stay nor constant monitoring can be beneficial. There are currently no methods nor devices to treat patient fluid overload by enhancing fluid decongestion through the skin.

There are several methods by which to promote fluid transfer through the skin. For example: Elevation of core temperature, however, it may be difficult for HF patients that will not tolerate the increase in core T heat; neural stimulation by drugs, although may not be tolerable for long durations; elevation of skin temperature, which is a preferred method by which to promote perspiration and be tolerable and even comfortable for the patients if subjected only to the lower part of the body from the chest down.

The skin starts to sweat at skin temperatures of usually over 33 degrees Celsius, but varies from one person to the other.

Accordingly, in some aspects, this disclosure provides both a method and apparatus for decongesting fluid overloaded patients by elevating and controlling partial body skin temperature to values over 36 degrees Celsius and typically between 37-39 degrees Celsius. These skin temperatures may enhance fluid flow from the edematous regions in the interstitial compartment to the eccrine sweat glands and out to the skin. Immediate evaporation of the sweat on the skin may be accomplished by the low humidity and continuous airflow that elevated the skin temperature. The evaporation process cools down also the blood flowing to the skin and upon its return to the deeper vasculature it ensures that the core body temperature remains within normal values. This effective treatment can be performed whilst maintaining core temperature values, HR and BP at baseline/normal levels.

In some aspects, this disclosure describes an apparatus that elevates partial body skin temperature by covering part of the patient with a loose and self-wearable fabric that is worn around the chest and upper back all the way down to the feet, preferably, including the toes. A tighter elastic band of up to about 5 cm wide or a tightening string, may be placed around the chest and lower back of the wearable fabric, and may be built in so as to eliminate any air flow in nor out towards the face and head from that region.

Figure 22:
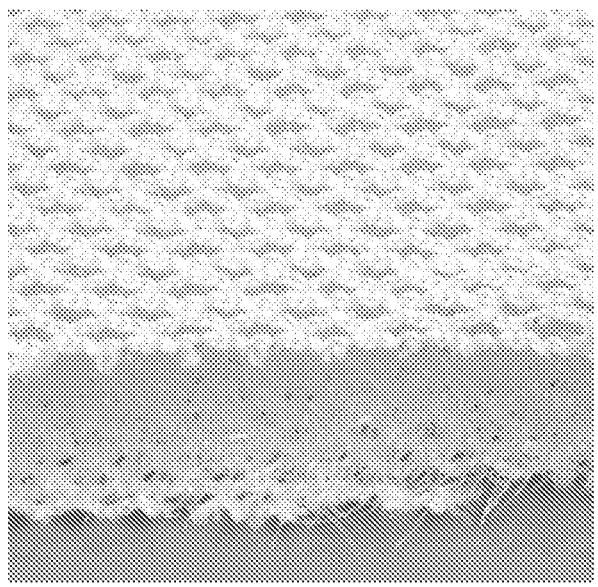
FIGS. 22 & 23 show a cross sectional view of a wearable apparatus of the invention.

The fabric may be made form a mesh, for example, as shown in FIG. 22. The mesh ensures flow of air to every region of the body thus enabling sweating and evaporation. Due to the mesh structure even when the patient is seated down, the patient may touch the wearable just at a very small region whilst around it the air still flows, elevates the skin temperature and evaporates the sweat when it flows out.

Preferably, there is an air inlet port and an air outlet port at opposite sides of the wearable. The inlet may be at the feet and the outlet may be at a level of the chest, or visa versa. Warm air from a heater may be directed into the wearable from the inlet port. The air can be diverted using smaller tubes to all parts of the body as can be seen from the FIG. 20. The warm air may heat up the skin temperature until it initiates sweating. The air may leave the wearable at higher humidity then its inlet humidity as it now has the sweat that evaporated from the skin in it. The air may evaporate the sweat very quickly as the relative humidity will always be kept below, for example, 40% at the inlet ensuring that also with maximal sweat rates at the outflow the humidity will not exceed, for example, 60%.

The warm air may initiate sweat when the skin temperature elevates above a certain temperature that varies slightly between one person to the other but in general may be above 32 degrees Celsius and below 36 degrees. Above this onset temperature the sweat rate may increases as the temperature elevates. To ensure that the skin does not start to burn, the temperature of the skin may be kept below 42 degrees Celsius.

In some aspects, the invention also provides an apparatus that comprises of a control unit and input sensors and meters, which may include any one or more of:

1. A skin temperature sensor placed on a part of the body that its temperature is being raised. It can be on the leg, abdomen, torso or back;
2. Two relative humidity and temperature sensors, placed one at the warm air inflow line and the second at the warm air outflow port. Online readings may be sent to the control unit that then calculates the absolute humidity form the relative humidity and temperature;
3. Air flow meter placed in the inflow line measuring continuously the air flow rate into the wearable. The online readings may be sent to the control unit;
4. A weight scale to measure the patient's weight before the procedure and at the end of the procedure. The weight sends the recording to the control unit;
5. A warm air heater that is set to deliver air at temperatures between about 37 degrees Celsius and 55 degrees Celsius and at relative humidity of up to 40% at 40 degrees Celsius; and
6. A control unit that receives input readings from the above sensors and meters calculates the sweat rates by subtracting the inlet from the outlet absolute humidity and then multiply by the air flow rate. The calculated sweat rate is then evaluated relative to the required sweat rate and the required weight loss.

In instances where the sweat rate is too low or too high or the relative humidity elevates above, for example 60%, the control unit may set the inflow air temperature and flow rate to meet the desired sweat rate and weight loss that's required per treatment and reduce the relative humidity to enable immediate evaporation. The control unit may also send the information and treatment parameters by the internet to the treating nurse or physician.

Figure 25:
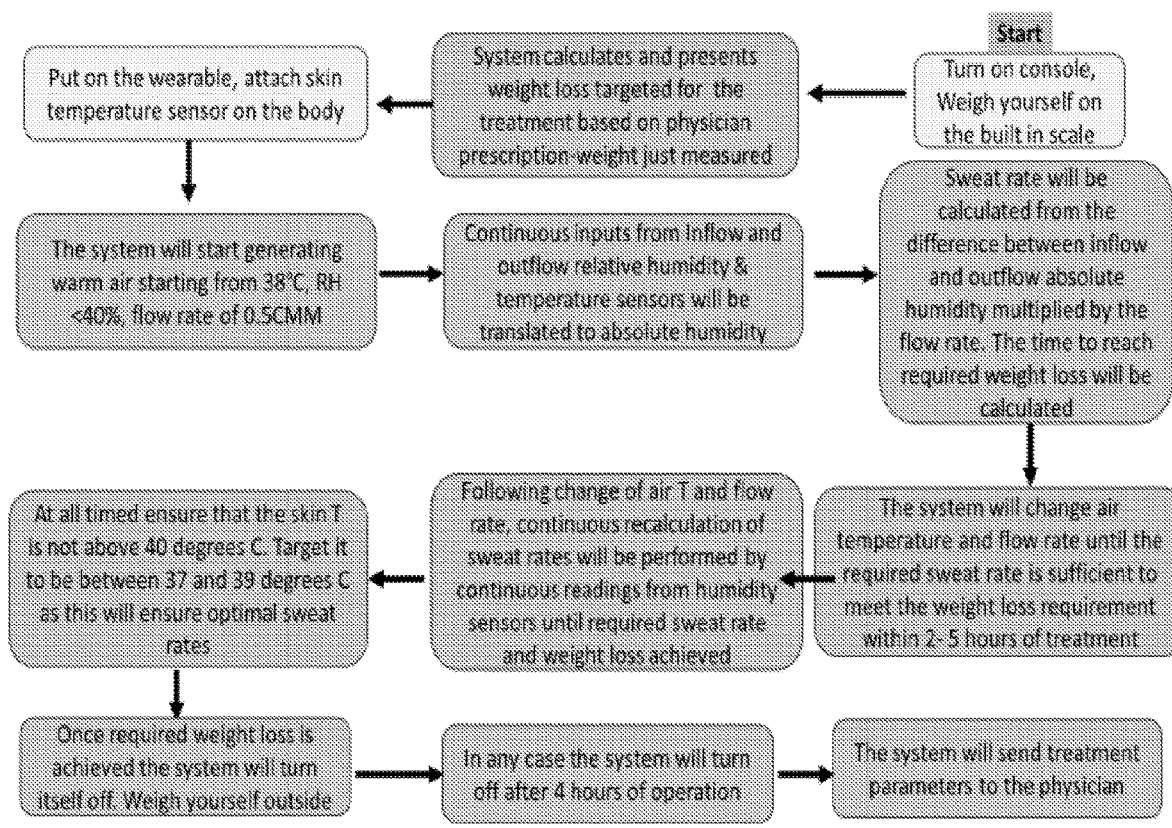
FIG. 25 shows a diagram of a system algorithm of the invention.

An algorithm executed by the control unit is presented in FIG. 25. The algorithm ensures that a treatment is set automatically with maximal safety and is thus suitable to, for example, an elderly patient that cannot operate devices that require complicated operation and thinking.

For example:

The patient is told that his target weight should be 80 kg.
The patient turns on the device and the target weight is being set in the set up screen or sent by the physician by the home wireless internet.
He weighs himself on the integrated system weight and he is 81 kg.
The system generates a signal or a voice telling the patient that he will be treated for 3-5 hours depending on the sweat rate.
The patient wears the wearable and the system automatically starts to send in warm air at 40° c. and relative humidity per the ambient air but less than 40% and at a flow rate of 0.5 cubic meter/minute (CMM)
The system measures the relative humidity and temperature at the outlet and inlet ports and calculates the sweat rate. For example, the calculated sweat rate is 150 ml/hr and the relative humidity is 75%. The system will increase the flow rate to reduce the humidity to less than 60% (to enable full evaporation, more efficient sweating and maintaining core temperature at normal levels).
If the skin temperature is below 37° c. the system will also elevate the input temperature until the skin T is above 38° c. but less than 40° c.
Once the system detects a sweat rate of 200 lml/hr and skin T between 37-39 degrees and relative humidity below 60% then the system will set these parameters and determine the treatment duration.
Once the calculated targeted weight is met the system stops the operation and the patient is asked to weigh again.

Figure 20:
FIG. 20 shows a side view of a wearable apparatus of the invention.

FIG. 20 shows a side view of a wearable apparatus according to aspects of the invention.

Figure 21:
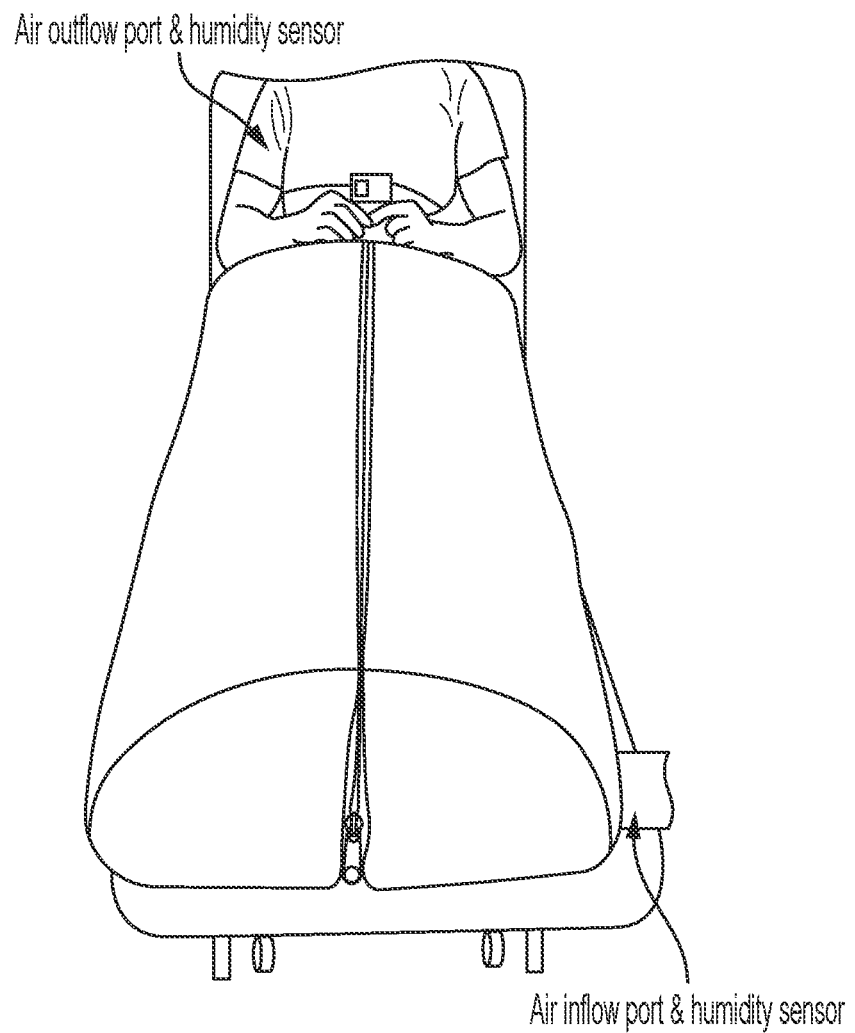
FIG. 21 shows a front view of a wearable apparatus of the invention.

FIG. 21 shows a front view of a wearable apparatus according to aspects of the invention. As depicted, air is dispersed and diverted to all parts of the body.

Figure 23:
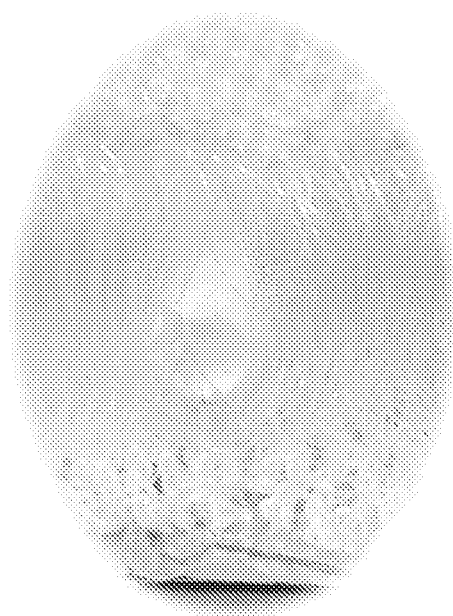

FIGS. 22 & 23 show a cross sectional view of a wearable apparatus. The cross section shows the mesh to lower contact area of patient. The tubing spreads the air to all body parts making the skin temperature homogenous.

Figure 24:
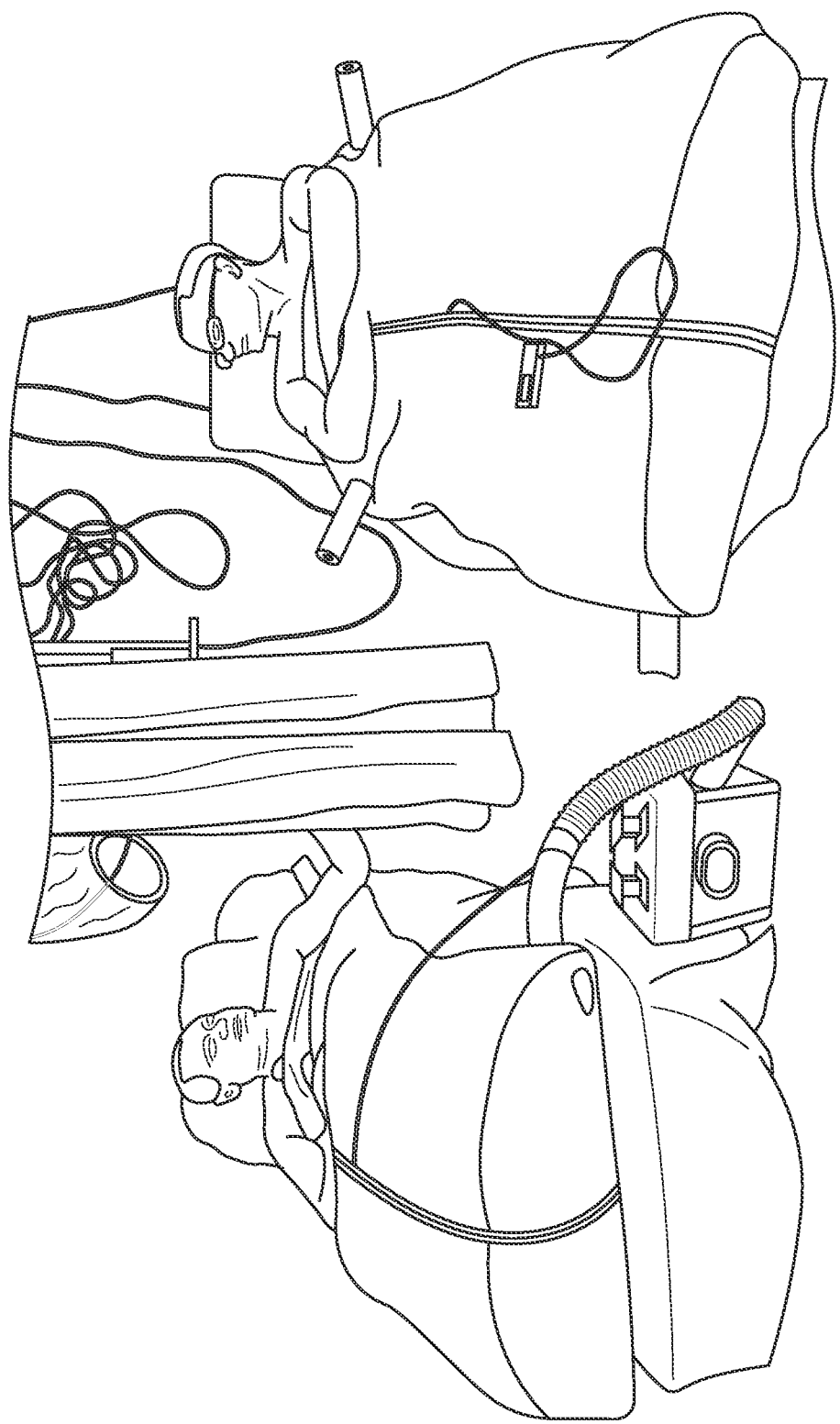
FIG. 24 shows another view of a wearable apparatus of the invention.

FIG. 24 shows another view of a wearable apparatus according to aspects of the invention.

FIG. 25 shows a diagraph of a system algorithm. In particular, FIG. 25 shows a built-in algorithm for enabling a safe and effective procedure.

The invention has been tested and proven to work as specified in human trials on healthy and fluid overloaded patients. The sweat rate of 9 consecutive treatments on 3 fluid overloaded patients resulted in an average fluid loss of 250 ml(gr)/hr. In 4 hours of treatment the weight loss was more than 1 Kg.

Figure 26:
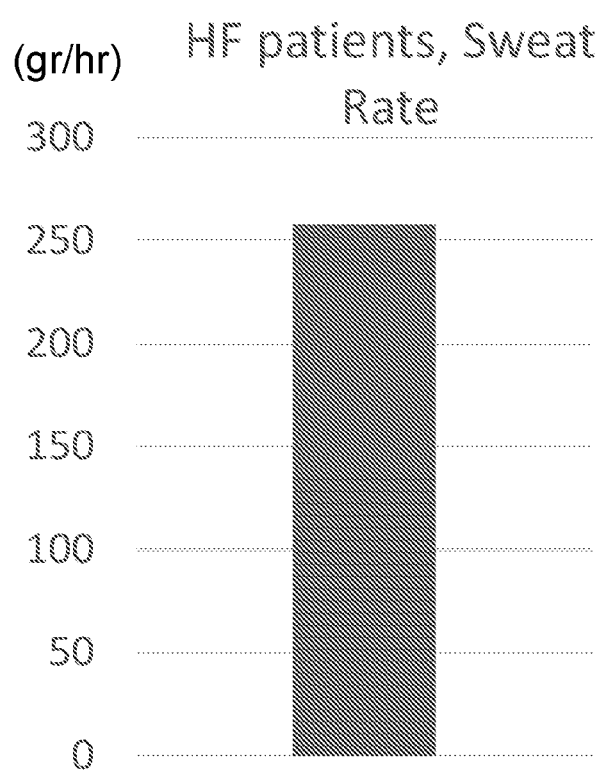
FIG. 26 shows results from 4 hours experiment on HF, fluid overloaded patients.

FIG. 26 shows results from 4 hours experiment on HF, fluid overloaded patients.

FIG. 27 shows an example of the calculation performed from the online humidity sensors and the air flow meter.

FIG. 28 shows results from the 3rd patient treated during his 3rd treatment. As it can be seen from the clinical results, the invention works and efficiently decongests, non-invasively, the fluid overload in patients.

Figure 29:
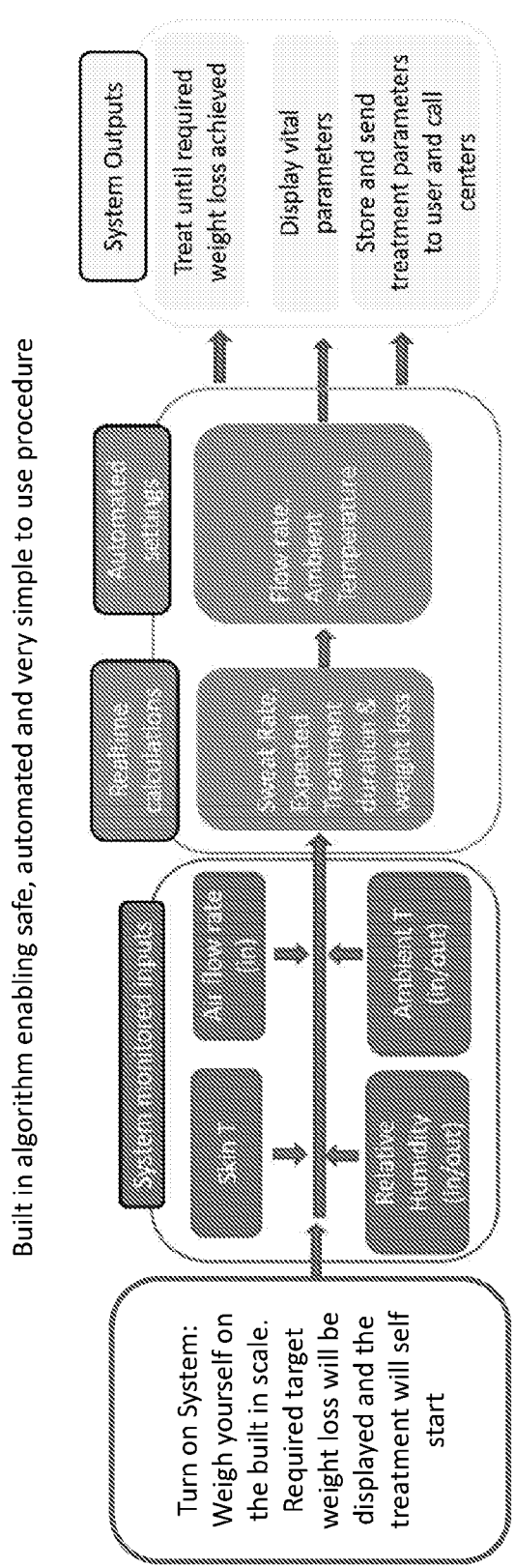
FIG. 29 shows a built-in algorithm executable by a counsel of the invention.

FIG. 29 shows a built-in algorithm executable by a counsel of the invention. The algorithm is designed to enable safe, automated and very simple use of procedure.

FIG. 30 shows clinical data from six treated subjects. The data relates to renal function tests.

Figure 31:
FIG. 31 shows treatment results from using systems and methods of the invention.

FIG. 31 shows treatment results. Shown are patient images taken before, during, and after a fluid removal treatment. As shown, treating a patient for Edema (swelling) by transferring fluids through the patient's skin, successfully alleviates swelling.

Figure 32:
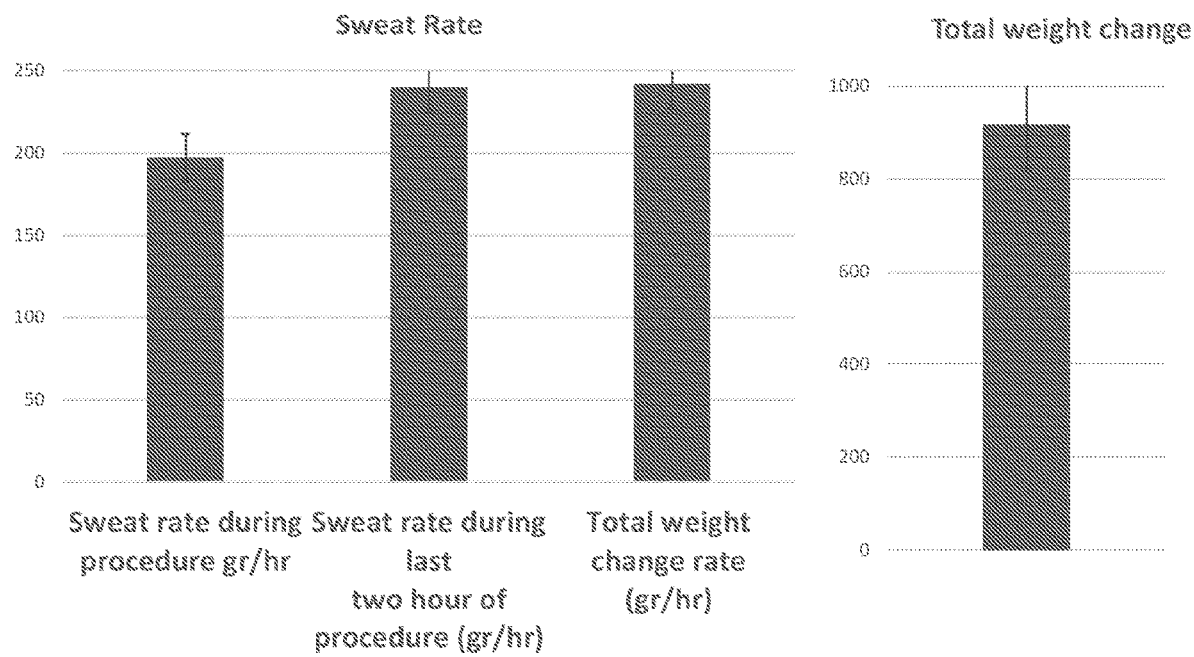
FIG. 32 shows clinical data from using systems and methods of the invention.

FIG. 32 shows clinical data. The data are taken from normal six subjects, e.g., not subjects suffering from heart failure. The data show changes in sweat rate during procedure and total weight loss as a result of treatment. Of note, the weight loss during treatment from sweating is approximately 200 gr/hr. During treatment, blood pressure, heart rate, core temperature, urine output, and blood electrolytes remained at baseline levels.

Figure 33:
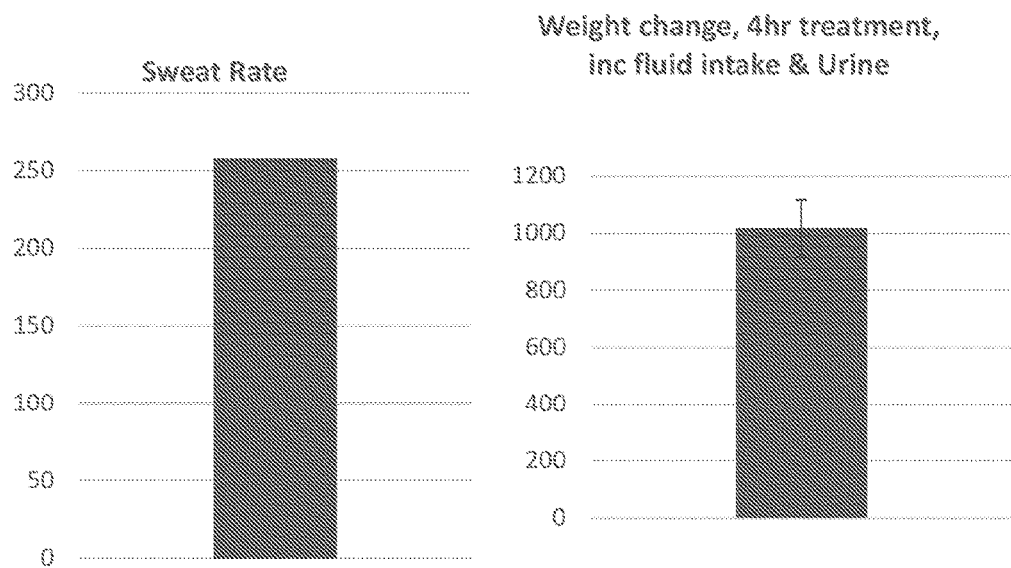
FIG. 33 shows clinical data from using systems and methods of the invention.

FIG. 33 shows clinical data. The data are taken from seven heart failure subjects. Of note, the weight loss from sweating was approximately 235 gr/hr. In 4 hours, net weight loss was approximately 1 Kg. During treatment, blood pressure, heart rate, core temperature, urine output, and blood electrolytes remained at baseline levels.

Figure 34:
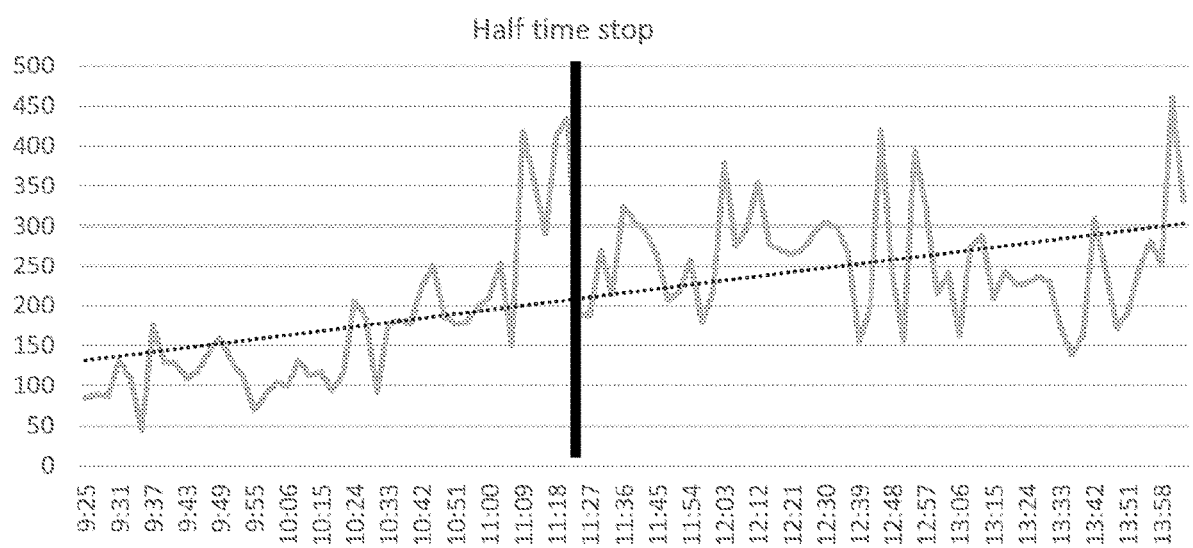
FIG. 34 shows clinical data from using systems and methods of the invention.

FIG. 34 shows data relating to sweat rate. The sweat rate (ml/hr) is calculated from humidity sensors, during patient treatments.

Accordingly, in some aspects, this disclosure provides a method for removing fluid overload from the interstitial and intravascular compartments by promoting their flow to the eccrine sweat glands and out to the skin by elevating partial body skin temperature only. Alternatively, or in addition to, this disclosure provides a method for controlling skin temperature and sweat rate by closing a control loop inputting relative humidity at the inflow and the outflow, the air flow rate and the skin temperature and changing the flow rate and inflow air temperature until a sufficient sweat rate is achieved. The apparatus may have a weight built in that inputs the baseline and final weights to the system that can then send the information, for example, by the internet, to the treating physician. The apparatus may be worn around a body part, for example, from the chest and upper back down to the feet and toes. The apparatus may enable free flow of air inside the apparatus and evaporate all the sweat as it increases the air flow rate to ensure that the relative humidity is less than 60%. The apparatus may have a cross section with a mesh fabric that contacts the skin at very small area thus enabling free flow and sweat evaporation in maximal areas. The apparatus may have an airflow dispersion system incorporated inside the mesh that spreads the air evenly in the wearable thus ensuring homogenous temperatures around the body and by such optimizing total sweat rate.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A fluid stimulation system comprising:
a mobile, wearable apparatus comprising a chamber sized to fit around a body part of a subject and to stimulate fluid loss in the subject, wherein the fluid is sweat, and wherein at least a portion of the chamber provides a clear volume of air between the body part and one or more walls of the chamber upon receipt of air flow and subsequent expansion of the chamber, the chamber comprising an inlet and an outlet and the chamber being configured such that an air flow passes through the chamber from the inlet to the outlet to thereby create a controlled environment around the body part of the subject for stimulating fluid loss in the subject;
first and second relative humidity and temperature sensors, wherein the first relative humidity sensor is operably located at the inlet and the second relative humidity sensor is operably located proximate the outlet; and
a controller configured to monitor and control conditions of the controlled environment around the body part of the subject, the controller being communicatively coupled with at least the first and second relative humidity and temperature sensors and configured to calculate a sweat rate within the chamber based, at least in part, on data received therefrom and control and adjust inflow air temperature and/or air flow rate into the chamber based, at least in part, on the calculated sweat rate.

2. The system of claim 1, wherein the air flow includes negative ions that are introduced by a component of the fluid stimulation system.

3. The system of claim 2, wherein the negative ions comprise one of bromide, chloride, fluoride, iodide, nitride, oxide, or sulfide ions.

4. The system of claim 3, wherein the component is one of a negative ion generator or an ion resin located at the inlet of the chamber.

5. The system of claim 1, wherein the controller is operable by a user to program conditions of the chamber.

6. The system of claim 1, further comprising a gas mixture with or without air.

7. The system of claim 1, further comprising an air fan and heat source coupled to the chamber.

8. The system of claim 7, further comprising an inflow flow meter associated with the air fan.

9. The system of claim 8, wherein the flow meter is communicatively coupled with the controller and data from the flow meter is used for calculation of the sweat rate within the chamber.

10. The system of claim 1, wherein the controller is used to analyze sweat content and recommend nutritional supplement.

11. The system of claim 1, wherein the body part comprises one or more legs, one or more arms, a torso, a lower back, an upper back, a chest or an abdomen.

12. The system of claim 11, wherein the abdomen comprises up to a chest level and below a heart level.

13. The system of claim 1, wherein an interior of the chamber is configured such that one or more walls of the chamber are kept spaced from the body part of the subject.

14. The system of claim 1, wherein one or more walls of the chamber have direct contact with the body part.

15. The system of claim 1, further comprising a skin temperature sensor.

16. The system of claim 1, wherein the controller is configured to control and adjust inflow air temperature and/or air flow rate into the chamber to maintain a sweat rate of between 50 milliliters per hour and 300 milliliters per hour until a desired fluid loss in the subject is attained.

17. A method for treating fluid overload in a subject, the method comprising:
    shifting fluids directly and non-invasively from an interstitial compartment of the subject to skin of the subject through controlled local fluid loss, thereby removing excess fluid from the interstitial compartment of the subject and treating fluid overload in the subject,
    wherein the fluid loss is sweating stimulated by controlling an environment within a chamber of a mobile, wearable apparatus fitted around a body part of a subject, said environment being monitored and controlled by a controller configured to control and adjust inflow air temperature and air flow rate into the chamber based, at least in part, on a calculated sweat rate within the chamber based, at least in part, on data received from one or more relative humidity sensors configured to capture relatively humidity data associated with the chamber.

18. The method of claim 17, further including introducing negative ions into the airflow to inhibit sodium re-absorption during sweating.

19. The method of claim 18, wherein the negative ions comprise one of bromide, chloride, fluoride, iodide, nitride, oxide, or sulfide ions.

20. The method of claim 17, further comprising aerobic or anaerobic exercising of a body part of the subject within the chamber to encourage sweating.

21. The method of claim 17, further comprising analyzing sweat content and recommending nutritional supplement.

22. The method of claim 17, wherein the method is carried out using a sweat stimulation system.

23. The method of claim 22, wherein the sweat stimulation system comprises:
    a chamber sized to fit around a body part of a subject, wherein at least a portion of the chamber provides a clear volume of air between the body part and one or more walls of the chamber upon receipt of air flow and subsequent expansion of the chamber, the chamber comprising an inlet and an outlet and the chamber being configured such that an air flow passes through the chamber from the inlet to the outlet to thereby create a controlled environment around the body part of the subject for stimulating sweating in the subject; and
    first and second relative humidity and temperature sensors, wherein the first relative humidity sensor is operably located proximate the inlet and the second relative humidity sensor is operably located proximate the outlet.

24. The method of claim 23, wherein the negative ions are introduced by one of a negative ion generator or an ion resin that is located at the inlet of the chamber.

25. The method of claim 17, wherein a plurality of sensors provides data to the controller for calculating sweat rate within the chamber.

26. The method of claim 17, further comprising controlling and monitoring conditions of the environment within the chamber using the controller, wherein the controller is operable by a user to program conditions of the chamber.

27. The method of claim 17, further comprising monitoring skin temperature of the subject and stopping operation of the system if the skin temperature exceeds 38° C.

28. The method of claim 17, wherein the controller is configured to control and adjust inflow air temperature and/or air flow rate into the chamber to maintain a sweat rate of between 50 milliliters per hour and 300 milliliters per hour until a desired fluid loss in the subject is attained.

* * * * *